(12) United States Patent
Dax

(10) Patent No.: US 11,161,826 B2
(45) Date of Patent: *Nov. 2, 2021

(54) MANUFACTURING METHODS AND POLYMORPHS OF A THIAZOLINE ANTI-HYPERALGESIC AGENT

(71) Applicant: ACADIA PHARMACEUTICALS INC., San Diego, CA (US)

(72) Inventor: Scott L. Dax, Landenberg, PA (US)

(73) Assignee: Acadia Pharmaceuticals Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/814,606

(22) Filed: Mar. 10, 2020

(65) Prior Publication Data

US 2020/0354328 A1 Nov. 12, 2020

Related U.S. Application Data

(60) Provisional application No. 62/846,096, filed on May 10, 2019.

(51) Int. Cl.
*C07D 277/18* (2006.01)

(52) U.S. Cl.
CPC ........ *C07D 277/18* (2013.01); *C07B 2200/13* (2013.01)

(58) Field of Classification Search
None
See application file for complete search history.

(56) References Cited

U.S. PATENT DOCUMENTS

| 4,785,008 | A | 11/1988 | Coquelet et al. |
| 5,840,739 | A | 11/1998 | Bergeron |
| 9,102,636 | B2 | 8/2015 | Mannion et al. |
| 2004/0242494 | A1 | 12/2004 | Brenchley et al. |

FOREIGN PATENT DOCUMENTS

| EP | 2498752 A2 | 9/2012 |
| EP | 3070084 A1 | 9/2016 |
| WO | 2006114274 A1 | 11/2006 |
| WO | 2008054292 A1 | 5/2008 |
| WO | 2011059324 A2 | 5/2011 |
| WO | 2011112602 A1 | 9/2011 |
| WO | 2018102726 A1 | 6/2018 |

OTHER PUBLICATIONS

"Chemistry Libretexts. 7.4: Effects of Solvent, Leaving Group, and Nucleophile on Unimolecular Substitution", https://chem.libretexts.org/Bookshelves/Organic_Chemistry/Map%3A_Org, accessed on Jul. 18, 2020, 2015, pp. 1-9.

Kuwano, et al., "Aqueous Hydroxide as a Base for Palladium-Catalyzed Amination of Aryl Chlorides and Bromides", J Org Chem, vol. 67, 2002, pp. 6479-6486.
Melikoglu, et al., "Does Neuropathic Pain Affect the Quality of Sleep?", Eurasian Journal of Medicine, vol. 49, 2017, pp. 40-43.
"Crystallization", Kirk-Othmer Encyclopedia of Chemical Technology, vol. 8, 2002, pp. 95-147.
Bernstein, "Polymorphism in Molecular Crystals", Clarendon Press, Oxford, X-Ray Crystallography, Analytical Techniques for Polymorphs, 2002, pp. 115-118.
Braga, et al., "Making crystals from crystals: a green route to crystal engineering and polymorphism", J Royal Soc Chem Chem Commun, 2005, pp. 3635-3645.
Davidovich, et al., "Detection of Polymorphism by Powder X-Ray Diffraction: Interference by Preferred Orientation", Am Pharm Rev, vol. 7, Issue 1, 2004, pp. 10, 12, 14, 16, 100.
Dean, et al., "Section 10", Analytical Chemistry Handbook, McGraw-Hill, Inc., 1995, pp. 10.24-10.26.
Esumi, et al., CAPlus AN 1994:260451; Document No. 120:260451, 1994.
Guillory, "Generation of Polymorphs, Hydrates, Solvates, and Amorphous Solids", Polymorphism in Pharmaceutical Solids (edited by Harry Brittain), NY: Marcel Dekker, Inc., vol. 1-2, 1999, pp. 183-226.
Ivanisevic, et al., "Uses of X-Ray Powder Diffraction in the Pharmaceutical Industry", Pharmaceutical Sciences Encyclopedia: Drug Discovery, Development, and Manufacturing, 2010, pp. 1-42.
Jain, et al., "Polymorphism in Pharmacy", Indian Drugs, vol. 23, No. 6, 1986, pp. 315-329.
Jordan, "Tamoxifen: A Most Unlikely Pioneering Medicine", Nature Reviews, vol. 2, 2003, pp. 205-213.
Morris, "Structural Aspects of Hydrates and Solvates", Polymorphism in Pharmaceutical Solids (edited by Harry Brittain), NY: Marcel Dekker, Inc., vol. 1-2, 1999, pp. 125-181.
Rothweiler, et al., "Luciferin and derivatives as a DYRK selective scaffold for the design of protein kinase inhibitors", European Journal of Medicinal Chemistry, vol. 94, Feb. 25, 2015, pp. 140-148.
Seddon, "Pseudopolymorph: A Polemic", Crystal Growth & Design, vol. 4, No. 6, 2004, pp. 1087 (2 pgs from internet).
Vippagunta, et al., "Crystalline Solids", Adv Drug Delivery Rev, vol. 48, 2001, pp. 3-26.
Yu, et al., "Physical characterization of polymorphic drugs: an integrated characterization strategy", PSTT, vol. 1, No. 3, Jun. 1998, pp. 118-127.

*Primary Examiner* — Samantha L Shterengarts
(74) *Attorney, Agent, or Firm* — Saul Ewing Arnstein & Lehr LLP; Domingos J. Silva; Dennis Ostrovsky

(57) ABSTRACT

Provided herein are methods of making a thiazoline anti-hyperalgesic, Compound 1, and polymorphs thereof. The methods described herein use inexpensive reagents and are capable of providing Compound 1 in commercial-scale quantities. Also provided are pharmaceutical compositions of Compound 1 suitable for human administration.

6 Claims, 10 Drawing Sheets

Cmp1 Imp-3 formed during HCl salt formation.

MANUFACTURING METHODS AND POLYMORPHS OF A THIAZOLINE ANTI-HYPERALGESIC AGENT

CROSS-REFERENCE TO RELATED APPLICATION

This application claims priority to U.S. Provisional Patent Application Ser. No. 62/846,096 entitled "MANUFACTURING METHODS AND POLYMORPHS OF A THIAZOLINE ANTI-HYPERALGESIC AGENT," filed May 10, 2019, the disclosure of which is incorporated herein by reference in its entirety.

BACKGROUND

Pain is defined as an unpleasant sensory and emotional experience. Pain, however, can be informative and useful. For example, nociceptive pain is often indicative of injury (e.g., tissue damage), and such pain typically evokes escape or protective behaviors in animals or in a human, in order to remove itself, or protect itself, from further exposure to the insult. However, inflammation, cellular and neuronal damage and other processes resulting from injury or disease can lead to states of chronic pathological pain. Hyperalgesia is a condition in which enhanced sensitivity to noxious stimuli is present, and thus the perception of pain is exaggerated. Allodynia is a condition in which normally non-noxious stimuli become painful. Persistent or chronic pain, manifested as hyperalgesia and/or allodynia, remains challenging to treat. Many patients do not respond to existing therapeutics, or have their pain poorly managed (i.e., inadequate relief), or experience relief of an inadequate duration.

Endogenous reactive species produced by injury, irritant and disease are key drivers of pain as can be demonstrated in animal models of hyperalgesia and allodynia. Reactive oxygen species (ROS) and reactive nitrogen species (RNS) include free radicals such as superoxide and hydroxyl radical, as well as the powerful oxidants peroxynitrite ($OONO^-$, also known as PN), and hydrogen peroxide ($H_2O_2$). Both peroxynitrite and hydrogen peroxide, generated in the periphery after injury, contribute to changes in excitability in sensory afferents.

Peroxynitrite has been implicated in the development of opiate-induced antinociceptive (pain) tolerance (tachyphylaxis) (Muscoli et al., 2007, J Clin Invest 117:3530-3539). Peroxynitrite results from the diffusion-controlled reaction of superoxide ($O_2^-$) and nitric oxide (NO). Unlike other endogenously produced reactive species/oxidants, peroxynitrite is not managed by enzymatic control. Peroxynitrite formation is facile, unleashing its powerful oxidative properties essentially unchecked, causing downstream effects that can cause pain.

In contrast, superoxide is formed from the action of NADPH oxidases and xanthine oxidase, and nitric oxide is produced by nitric oxide synthases (NOS). Hydrogen peroxide is formed from superoxide and the action of superoxide dismutase. During cellular stress (e.g., inflammation, nerve injury, ischemia), the action of these enzymatic systems can cause nitric oxide, superoxide and peroxide levels to increase significantly, which can lead to neuronal damage, hyperalgesia and allodynia. Concomitant increases in nitric oxide and superoxide can lead to greatly increased localized increases in peroxynitrite, which is capable of nitrating tyrosine residues within proteins, cross-linking cysteine residues and disrupting glutathione-disulfide homeostasis. Collectively, these effects lead to neuronal sensitization and pain, including neuropathic pain.

Diabetes is a leading cause of neuropathy. Approximately 50% of diabetic patients will develop peripheral neuropathy, which manifests as burning, excruciating, stabbing, or intractable types of pain. The currently available therapeutics are palliative, effective in only a portion of patients in providing symptomatic relief, and are not disease-modifying (diabetes). More troubling, even patients who initially experience relief from a given therapeutic usually revert to a painful state over time. Anticonvulsants such as pregabalin, gabapentin, and lamotrigine, and older tricyclic antidepressants (TCA) such as carbamazepine can be effective but are prone to produce CNS-associated adverse effects (e.g., sedation, cognitive deficits, and so forth). Antidepressants belonging to the norepinephrine- and/or serotonin-reuptake inhibitors (SNRIs) class such as duloxetine are useful alternatives in some patients. The use of opioids and non-steroidal anti-inflammatory drugs (NSAIDs) are commonplace but not preferable due to abuse potential, withdrawal, tolerance leading to dose-escalation, constipation, nausea, vomiting, and respiratory depression well-known to occur with opioid therapy, and gastrointestinal ulceration and nephrotoxicity associated with NSAID usage. Lastly, topical agents (capsaicin, topical nitrates, and topical TCAs) and local anesthetics have been used with mixed results.

Collectively, the treatment of painful diabetic neuropathy remains poorly managed as evident by Numbers-Needed-to-Treat values which range from 5 to 6 for the mostly widely used drugs (NEURONTIN®, LYRICA®, CYMBALTA®) (Treatment of Painful Diabetic Neuropathy, Ther. Adv. Chronic Dis. 2015, 6 (1) 15 (S Javed).

Post-operative pain is another source of pain that needs better treatment options than exist today. Post-operative pain is frequently the result of surgery, but other treatments such as, for example, management of acute pain following burns or non-surgical trauma can also result in severe pain. Post-operative pain management is important to reduce or eliminate pain and discomfort so that the surgical patient can begin ambulating as soon as possible, which speeds recovery.

The surgical site has a marked effect on the degree of post-operative pain. In general, surgery on the thorax and upper abdomen are more painful than surgery on the lower abdomen, which in turn is more painful than peripheral surgery on the limbs. In particular, thoracic surgery or upper abdominal surgery can produce extensive changes in pulmonary function, a decrease in abdominal muscle tone, and a related decrease in diaphragmatic function. Decreased function in the diaphragm can produce an inability to cough and clear mucus, which can lead to lung collapse and/or pneumonia. Persistent pain can reduce physical activity and mobility and lead to increased risk of deep vein thrombosis and pulmonary embolisms. These problems are unpleasant or even life-threatening and often result in extended hospital stays. Patients that have moderate to severe post-surgical pain frequently require pain control at least in the first 3 days after trauma or surgery, and often as much as 2 to 3 weeks post-surgery.

There is thus a need in the medical and patient communities for a new class of therapeutic agents that can relieve a wide range of pain, including, but not limited to, painful diabetic neuropathy and post-surgical pain. The methods and compounds described herein address this pressing need.

BRIEF DESCRIPTION OF THE FIGURES

The drawings illustrate generally, by way of example, but not by way of limitation, various embodiments of the present invention.

DETAILED DESCRIPTION OF THE INVENTION

Figure 1:
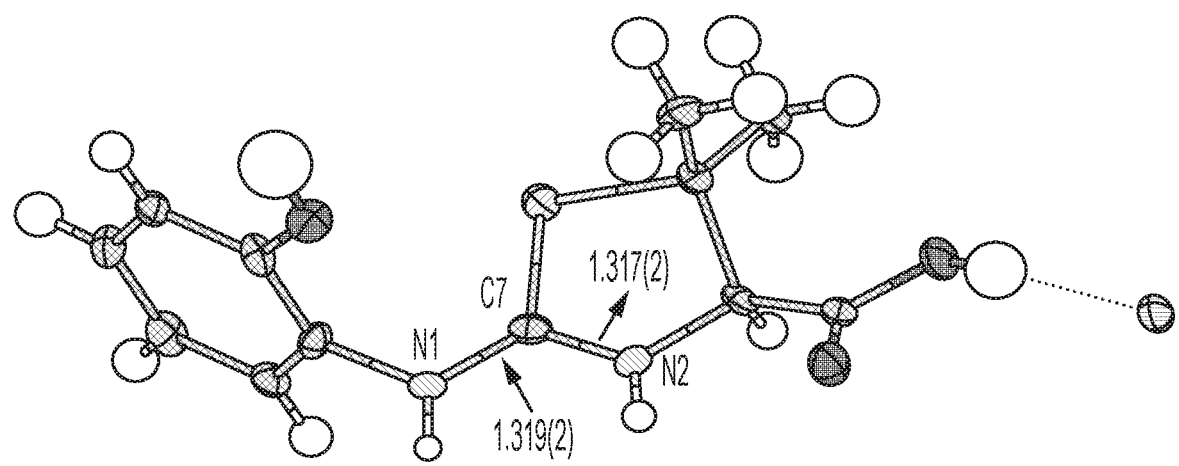
FIG. 1 is an X-ray crystal structure of (R)-2-(2-hydroxyphenylamino)-5,5-dimethyl-4,5-dihydrothiazole-4-carboxylic acid mono-hydrochloride (Compound 1), in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Definitions

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "solvent" as used herein refers to a liquid that can dissolve a solid, liquid, or gas. Non-limiting examples of solvents are silicones, organic compounds, water, alcohols, ionic liquids, and supercritical fluids.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "room temperature" as used herein refers to a temperature of about 15° C. to 28° C.

The term "standard temperature and pressure" as used herein refers to 25° C. and 101 kPa.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect (Emax) achieved within an assay.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids or bases, including inorganic acids or bases, organic acids or bases, solvates, hydrates, or clathrates thereof.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Salts may also include internal salts in which a molecule possesses both a positive and negative charge, known as zwitterions.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "potency" refers to the dose needed to produce half the maximal response ($ED_{50}$).

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein or a symptom of a condition contemplated herein, with the purpose to cure, heal, alleviate, relieve, alter, remedy, ameliorate, improve or affect a condition contemplated herein, or the symptoms of a condition contemplated herein. Such treatments may be specifically tailored or modified, based on knowledge obtained from the field of pharmacogenomics.

Preparation of Compounds of the Invention

The compounds described herein can be prepared by the general schemes described herein, using the synthetic method known by those skilled in the art. The following examples illustrate non-limiting embodiments of the invention.

The compounds described herein can possess one or more stereocenters, and each stereocenter can exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides, S-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water and ethanol. In other embodiments, the compounds described herein exist in unsolvated form.

In certain embodiments, the compounds of the invention may exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}c$, $^{13}c$, $^{14}c$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl (including phenolic), amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and tert-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as tert-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile tert-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

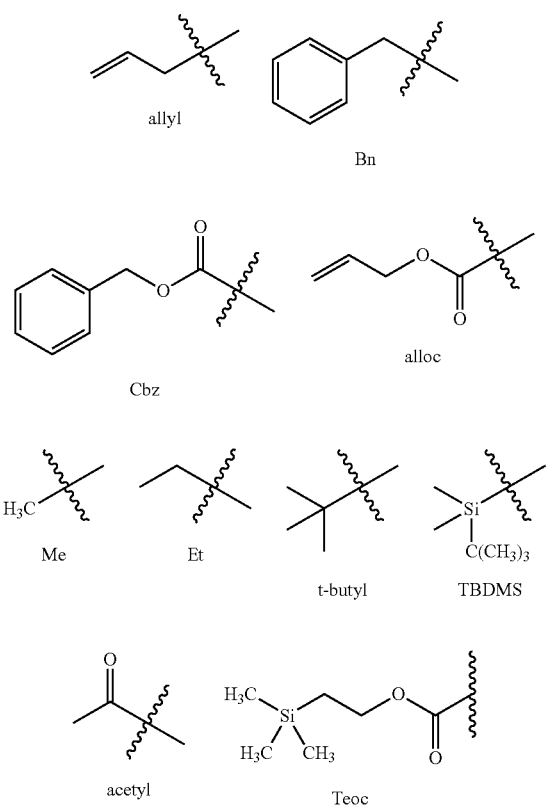

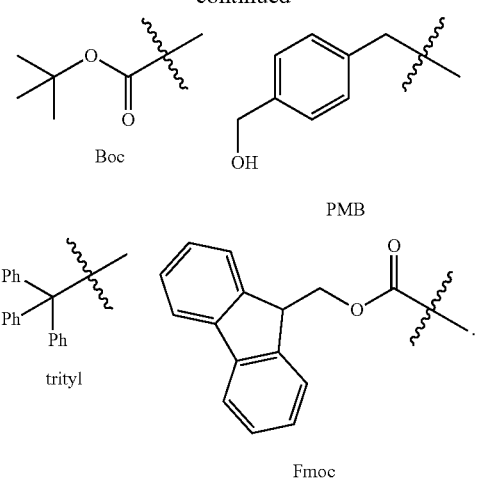

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Method of Manufacturing

A method of making a compound of Formula I (Compound 1) is provided.

Formula I (Compound 1)

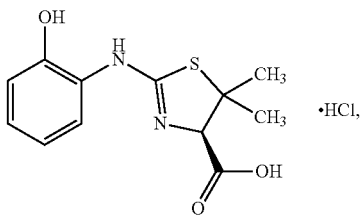

The method includes reacting an amine compound with a structure of:

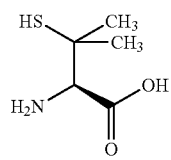

with

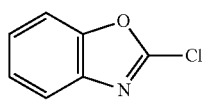

in the presence of a base and a first solvent to form an intermediate product of Formula II:

Formula II

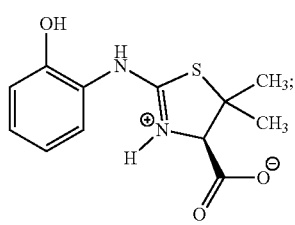

(Compound 1 Zwitterion)

and contacting the intermediate product with an acid and a second solvent to form Compound 1.

In various embodiments, Compound 1 can be prepared according to Scheme 1 as follows:

Scheme 1

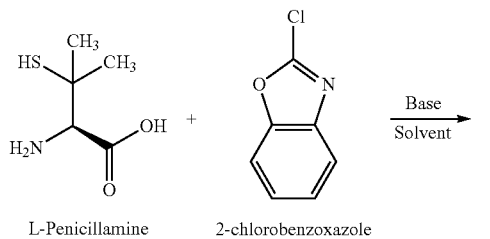

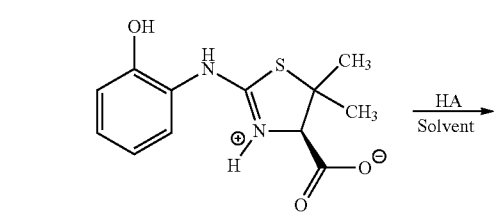

Compound 1

In various embodiments, Compound 1 Zwitterion is isolated prior to being treated with acid. The formal name of Compound 1 Zwitterion is (R)-2-((2-hydroxyphenyl)amino)-5,5-dimethyl-4,5-dihydrothiazol-3-ium-4-carboxylate. The isolation can be carried out by methods known in the art such as re-crystallization or precipitation from a suitable solvent, such as iso-propanol, in which Compound 1 Zwitterion is insoluble or sparingly soluble.

Compound 1 Zwitterion can be prepared, in various embodiments, according to Scheme 2:

Scheme 2

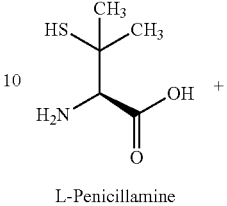 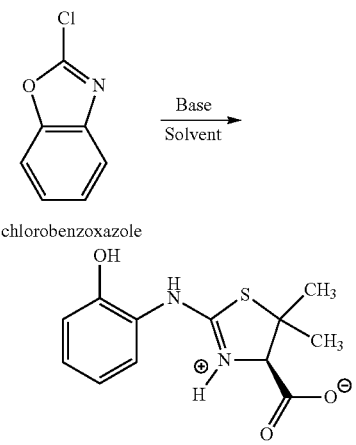

L-Penicillamine    2-chlorobenzoxazole

Compound 1 Zwitterion

In various embodiments, isolated Compound 1 Zwitterion can be converted to Compound 1 according to Scheme 3:

Scheme 3

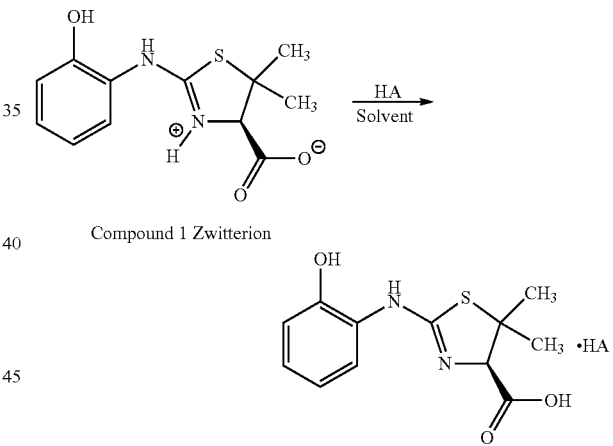

Compound 1

In Scheme 1 and Scheme 3, HA represents a protic acid, and A⁻ represents the conjugate base of HA.

The base in Scheme 1 can be any suitable base such as, without limitation, a primary, secondary, or tertiary amine, an alkyl lithium, a Grignard reagent, or an alkali metal hydroxide. In various embodiments, the base is selected from the group consisting of LiOH, NaOH, KOH, and combinations thereof. In various embodiments, the base is NaOH.

The first solvent can be any suitable solvent that is capable of dissolving the starting materials. The first solvent can be, in various embodiments, a polar protic solvent, a polar aprotic solvent, or any combination thereof. Suitable polar protic solvents can be, in various embodiments, water, methanol, ethanol, trifluoroethanol, iso-propanol, and mixtures thereof. In various embodiments, the polar aprotic solvent can be acetone, tetrahydrofuran, dimethylsulfoxide, acetonitrile, N,N-dimethylformamide, N-methyl-2-pyrrolidone, and mixtures thereof. The first solvent can also be a mixture of a protic polar solvent and an aprotic polar solvent, in any suitable ratio, such as from about 1:1 (protic:aprotic) to about 1:10 (protic:aprotic), or about 10:1 (protic:aprotic). In various embodiments, the first solvent is water.

The acid can be any suitable inorganic acid, such as HF, HCl, HBr, $H_2SO_4$, $HNO_3$, $H_3NSO_3$, $H_3PO_4$, and the like. The acid can also be an organic acid, such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like. In various embodiments, the acid is hydrochloric acid (HCl).

The second solvent can be any suitable solvent that is capable of dissolving polar substances such as Compound 1 Zwitterion. The second solvent can be, in various embodiments, a polar protic solvent, a polar aprotic solvent, or any combination thereof. Suitable polar protic solvents can be, in various embodiments, water, methanol, ethanol, trifluoroethanol, iso-propanol, and mixtures thereof. In various embodiments, the polar aprotic solvent can be acetone, tetrahydrofuran, dimethylsulfoxide, acetonitrile, N,N-dimethylformamide, N-methyl-2-pyrrolidone, and mixtures thereof. The second solvent can also be a mixture of a protic polar solvent and an aprotic polar solvent, in any suitable ratio, such as from about 1:1 (protic:aprotic) to about 1:10 (protic:aprotic), or about 10:1 (protic:aprotic). In various embodiments, the second solvent is iso-propanol.

Although Compound 1 is a hydrochloride acid addition salt, other pharmaceutically acceptable acid addition salts can be used in the methods described herein. Pharmaceutically-acceptable acids refers to those acids that are not toxic or otherwise biologically undesirable. Pharmaceutically acceptable acid addition salts can be formed with pharmaceutically acceptable inorganic acids including, but not limited to, hydrobromic acid, sulfuric acid, sulfamic acid, nitric acid, phosphoric acid, and the like.

Pharmaceutically acceptable acid addition salts can also be formed with pharmaceutically acceptable organic acids. Examples of pharmaceutically-acceptable organic acids, include but are not limited to, acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like. The methods can be used to economically scale the preparation of Compound 1 to commercial-scale operations if desired. The methods advantageously use inexpensive and environmentally benign reagents to produce Compound 1.

Physical Properties of Compound 1

Compound 1, (R)-2-(2-hydroxyphenylamino)-5,5-dimethyl-4,5-dihydrothiazole-4-carboxylic acid mono-hydrochloride, has the structure of Formula I:

Formula I

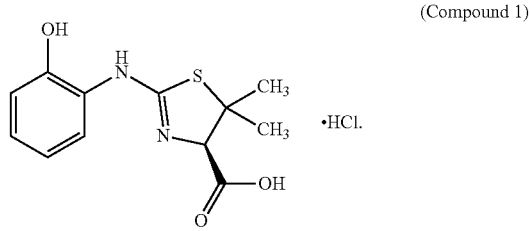

(Compound 1)

Compound 1 has the following pKa values: 2.29±0.02 (Acidic), 6.97±0.01 (Basic), and 10.24±0.03 (Acidic). Compound 1 is freely soluble in methanol and tert-butyl alcohol: water (1:1). Compound 1 is sparingly soluble in iso-propanol, ethanol, 10% water:iso-propyl acetate, 10% water/tetrahydrofuran, and water. Compound 1 is less than sparingly soluble in n-heptane, toluene, acetone, tetrahydrofuran, ethyl acetate, iso-propyl acetate, tert-butyl methyl ether, and tert-butyl alcohol.

Compound 1 has a Log D distribution coefficient at pH 7.2 of −0.07 (3 mL PBS Buffer: 1 mL Octanol) and −0.39 (2 mL PBS Buffer: 2 mL Octanol), where PBS is phosphate buffer solution.

FIG. 1 shows the X-ray crystal structure of Compound 1. The crystallographic parameters for the structure in FIG. 1 are listed in Table 1 below.

TABLE 1

Crystal Data for (R)-2-(2-hydroxyphenylamino)-5,5-dimethyl-4,5-dihydrothiazole-4-carboxylic acid mono-hydrochloride

| Crystal System | Orthorhombic |
| --- | --- |
| Space Group | P212121 |
| Unit Cell Dimensions | a = 7.00762(9) Å α = 90° |
| | b = 10.08020 (10) Å β = 90° |
| | c = 20.5203(2) Å γ = 90° |
| | Volume = 1449.52(3) Å3 |
| Goodness of Fit on F2 | 1.046 |
| Z' | 4 |

Figure 2:
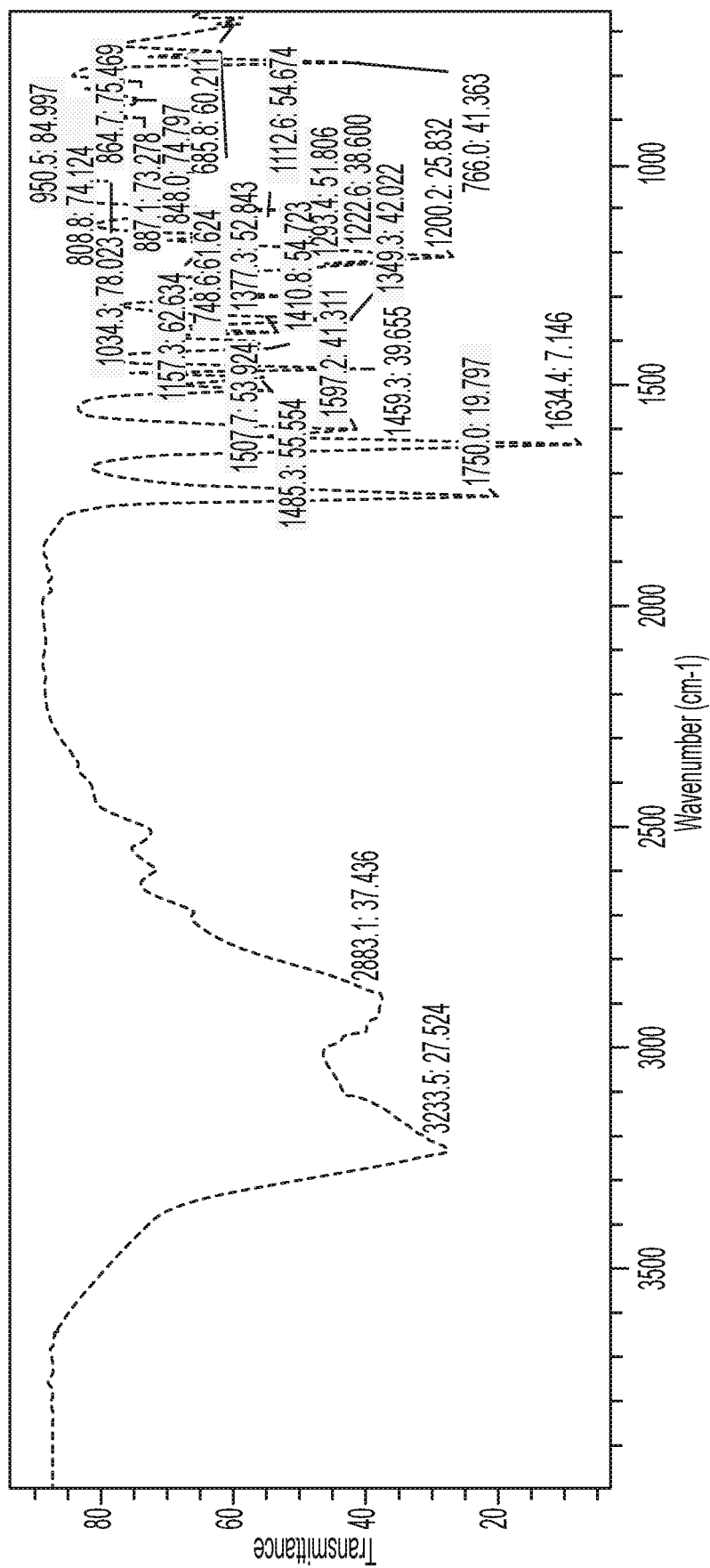
FIG. 2 is an infrared (IR) spectrum of Compound 1, in accordance with various embodiments.

Table 2 lists the peak assignments of the functional groups in Compound observed in the infrared spectrum of Compound 1 (FIG. 2).

TABLE 2

Interpretation of (R)-2-(2-hydroxyphenylamino)-5,5-dimethyl-4,5-dihydrothiazole-4-carboxylic acid mono-hydrochloride IR Data

| Range of Absorption (cm$^{-1}$) | Functional Group | Intensity | Type of Vibrations |
|---|---|---|---|
| *3200-3300 | N—H (Amine) | Broad | N—H Stretching |
| 2830-3000 | O—H (Acid) | Very broad | O—H Stretching |
| 1690-1750 | C=O (Carbonyl) | Sharp | C=O Stretching |
| 1590-1650 | C=N | Sharp | C=N Stretching |
| 1400-1600 | C=C | Medium | C=C Stretching (Aromatic) |

Figure 3:
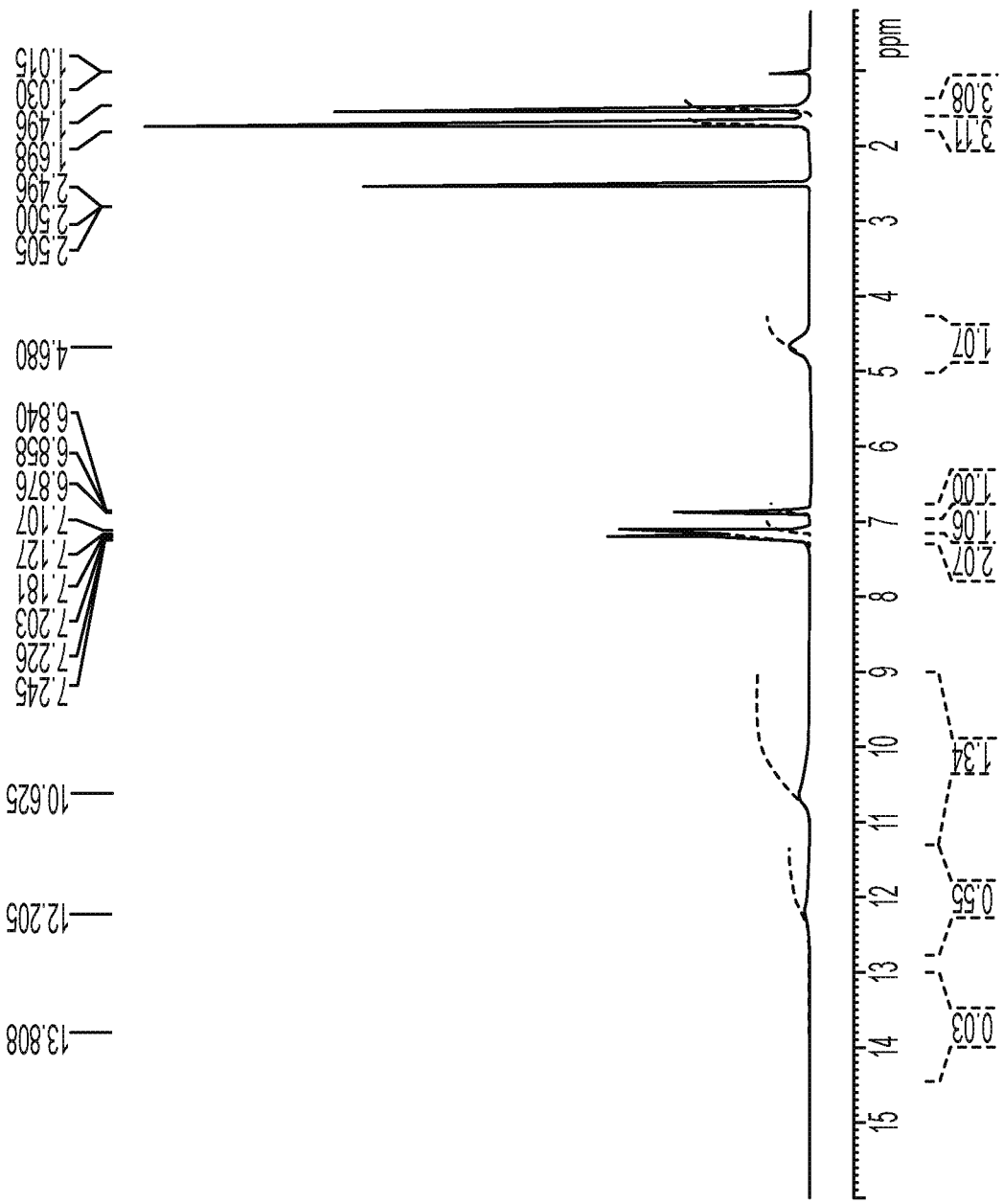
FIG. 3 is a $^1$H-NMR (nuclear magnetic resonance) spectrum of Compound 1, in accordance with various embodiments.

Table 3 lists the peak assignments for the hydrogen nuclei in the $^1$H NMR spectrum of Compound 1 (FIG. 3).

TABLE 3

Interpretation of $^1$H-NMR Spectrum of (R)-2-(2-hydroxyphenylamino)-5,5-dimethyl-4,5-dihydrothiazole-4-carboxylic acid mono-hydrochloride

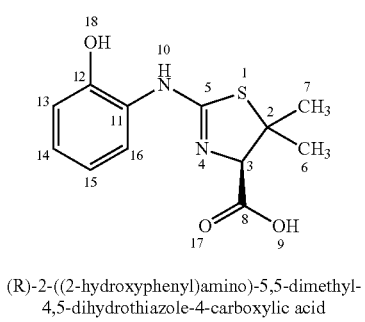

(R)-2-((2-hydroxyphenyl)amino)-5,5-dimethyl-4,5-dihydrothiazole-4-carboxylic acid

| Chemical Shift (ppm) | Multiplicity | Proton Number | Total Proton Integration |
|---|---|---|---|
| 12.205 | Broad singlet | OH | 1 |
| 10.625 | Broad singlet | NH | 1 |
| 7.245-7.181 | multiplet | 14&16 | 2 |
| 7.127-7.107 (J = 8) | doublet | 13 | 1 |
| 6.876-6.840 (J = 7.2) | triplet | 15 | 1 |
| 4.680 | singlet | 3 | 1 |
| 1.698 | Singlet | 6 | 3 |
| 1.496 | Singlet | 7 | 3 |

Figure 4:
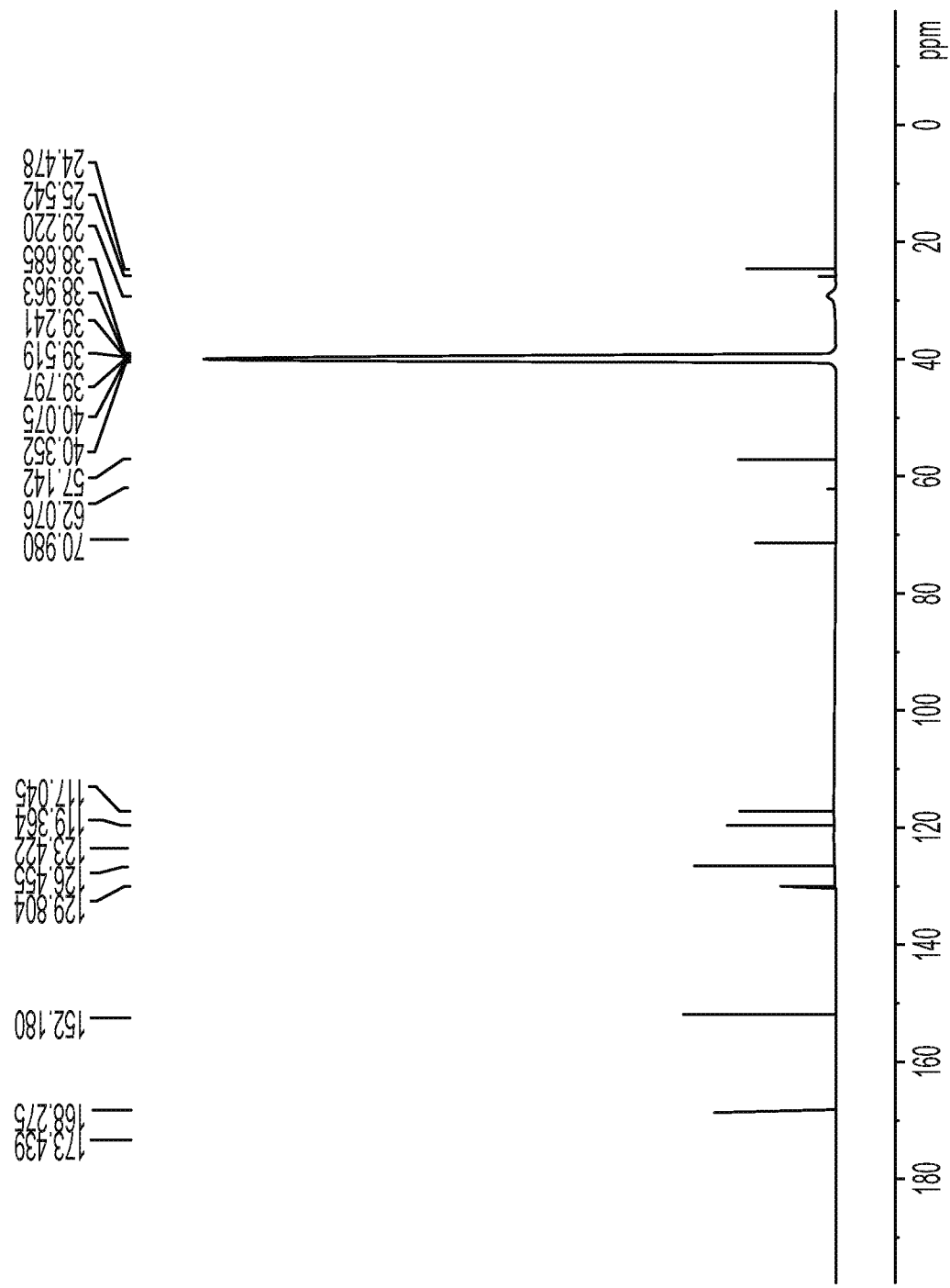
FIG. 4 is a $^{13}$C-NMR spectrum of Compound 1, in accordance with various embodiments.

Table 4 lists the peak assignments for the carbon nuclei in the $^{13}$C NMR spectrum of Compound 1 (FIG. 4).

TABLE 4

Interpretation of $^{13}$C-NMR Spectrum of (R)-2-(2-hydroxyphenylamino)-5,5-dimethyl-4,5-dihydrothiazole-4-carboxylic acid mono-hydrochloride

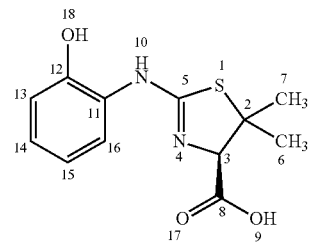

(R)-2-((2-hydroxyphenyl)amino)-5,5-dimethyl-4,5-dihydrothiazole-4-carboxylic acid

| Chemical Shift (ppm) | Assignment | Number of Carbons | Type of Carbon |
|---|---|---|---|
| 24.48 | 6 | 1 | Primary |
| 29.22 | 7 | 1 | Primary |
| 57.14 | 2 | 1 | Quaternary |
| 70.98 | 3 | 1 | Tertiary |
| 117.05 | 13 | 1 | Tertiary |
| 119.36 | 15 | 1 | Tertiary |
| 123.42 | 11 | 1 | Quaternary |
| 126.46 | 16 | 1 | Tertiary |
| 129.80 | 14 | 1 | Tertiary |
| 152.18 | 12 | 1 | Quaternary |
| 168.28 | 8 | 1 | Quaternary |
| 173.44 | 5 | 1 | Quaternary |

Additional characteristics of Compound 1 and related compounds are described in U.S. Pat. No. 9,102,636, which is hereby incorporated by reference in its entirety.

Polymorphs of Compound 1

Polymorphic screening of crystalline Compound 1 was performed using 15 organic/aqueous solvent systems, including: n-heptane, methanol, toluene, acetone, tetrahydrofuran, iso-propanol, ethanol, ethyl acetate, iso-propyl acetate, tert-butylmethyl ether, 10% water/90% iso-propyl alcohol, 10% water/90% tetrahydrofuran, tert-butyl alcohol, water, and 1:1 tert-butyl alcohol:water.

Figure 5:
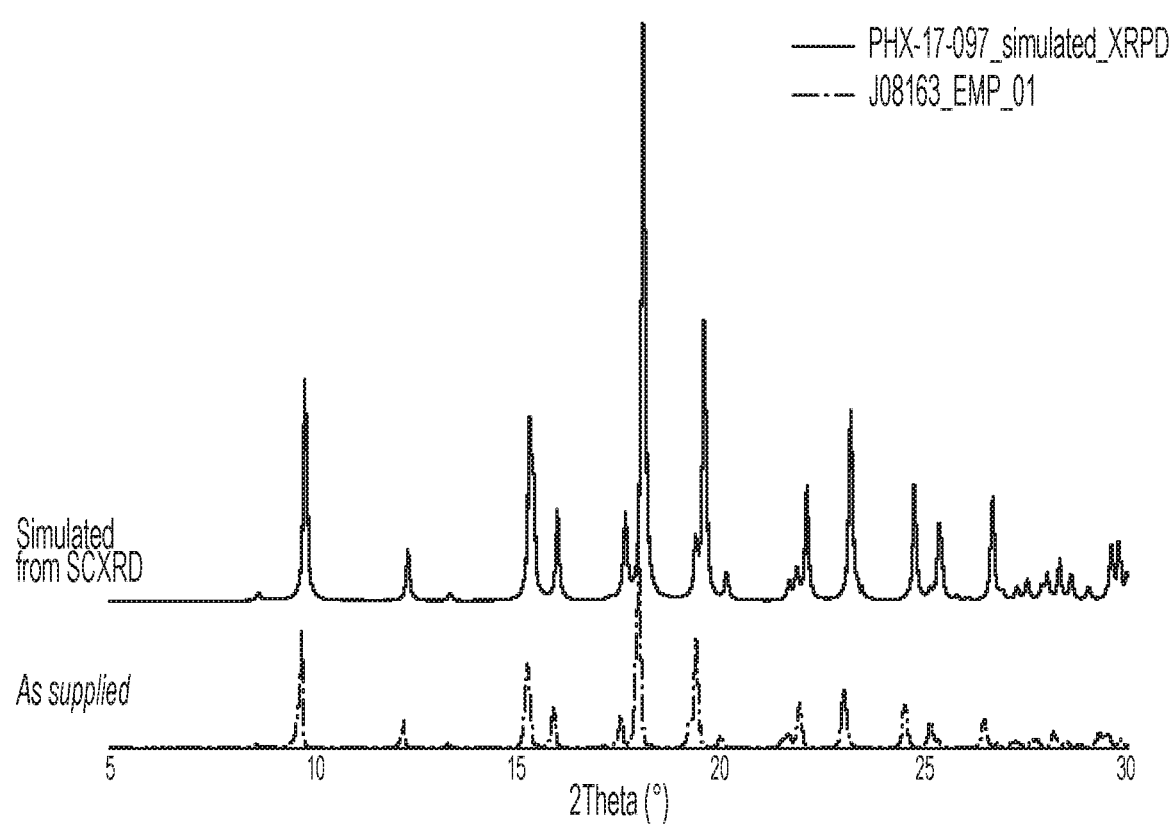
FIG. 5 is an experimental (bottom trace) and calculated XRPD (X-ray powder diffraction) trace (top trace) for Compound 1, in accordance with various embodiments.

Only one crystalline form was obtained (Form 1). Compound 1 is a non-solvated, crystalline, mono-hydrochloride salt. FIG. 5 shows the experimentally obtained XPRD spectrum of Compound 1 in the bottom trace, and the simulated XPRD spectrum in the top trace. The XPRD spectrum was measured using Cu Kα radiation and collected from 2 to 42 degrees 2θ. The experimentally obtained XPRD spectrum of Compound 1 has the following peaks and associated intensities:

| Angle (2θ ± 0.2) | Intensity % |
|---|---|
| 9.6 | 43.3 |
| 12.2 | 10.7 |
| 13.3 | 4.5 |
| 15.2 | 37.6 |
| 15.8 | 19.9 |
| 17.5 | 18.7 |
| 18.0 | 100.0 |
| 19.2 | 14.8 |
| 19.4 | 66.6 |
| 20.0 | 8.3 |
| 21.5 | 7.2 |
| 21.7 | 12.6 |

-continued

| Angle (2θ ± 0.2) | Intensity % |
|---|---|
| 21.9 | 31.0 |
| 23.0 | 47.6 |
| 24.5 | 25.2 |
| 25.1 | 18.6 |
| 25.2 | 6.9 |
| 26.4 | 21.2 |
| 26.7 | 4.1 |
| 27.1 | 5.4 |
| 27.2 | 6.4 |
| 27.7 | 8.1 |
| 28.1 | 13.2 |
| 28.4 | 6.7 |
| 28.8 | 4.1 |
| 29.2 | 15.1 |
| 29.4 | 15.1 |
| 29.7 | 6.0 |
| 30.1 | 12.3 |
| 30.5 | 12.2 |
| 31.1 | 13.8 |
| 31.4 | 26.6 |
| 31.9 | 11.4 |
| 32.8 | 7.6 |
| 34.0 | 15.5 |
| 34.5 | 7.5 |
| 35.1 | 4.8 |
| 35.4 | 6.6 |
| 35.7 | 5.0 |
| 36.4 | 6.9 |
| 36.9 | 3.8 |
| 37.5 | 13.8 |

-continued

| Angle (2θ ± 0.2) | Intensity % |
|---|---|
| 37.7 | 8.3 |
| 38.0 | 4.8 |
| 38.5 | 6.6 |
| 39.0 | 5.6 |
| 39.3 | 15.5 |
| 39.7 | 3.1 |
| 40.3 | 5.1 |
| 40.6 | 5.4 |
| 40.7 | 5.3 |
| 41.5 | 6.7 |

Figure 6:
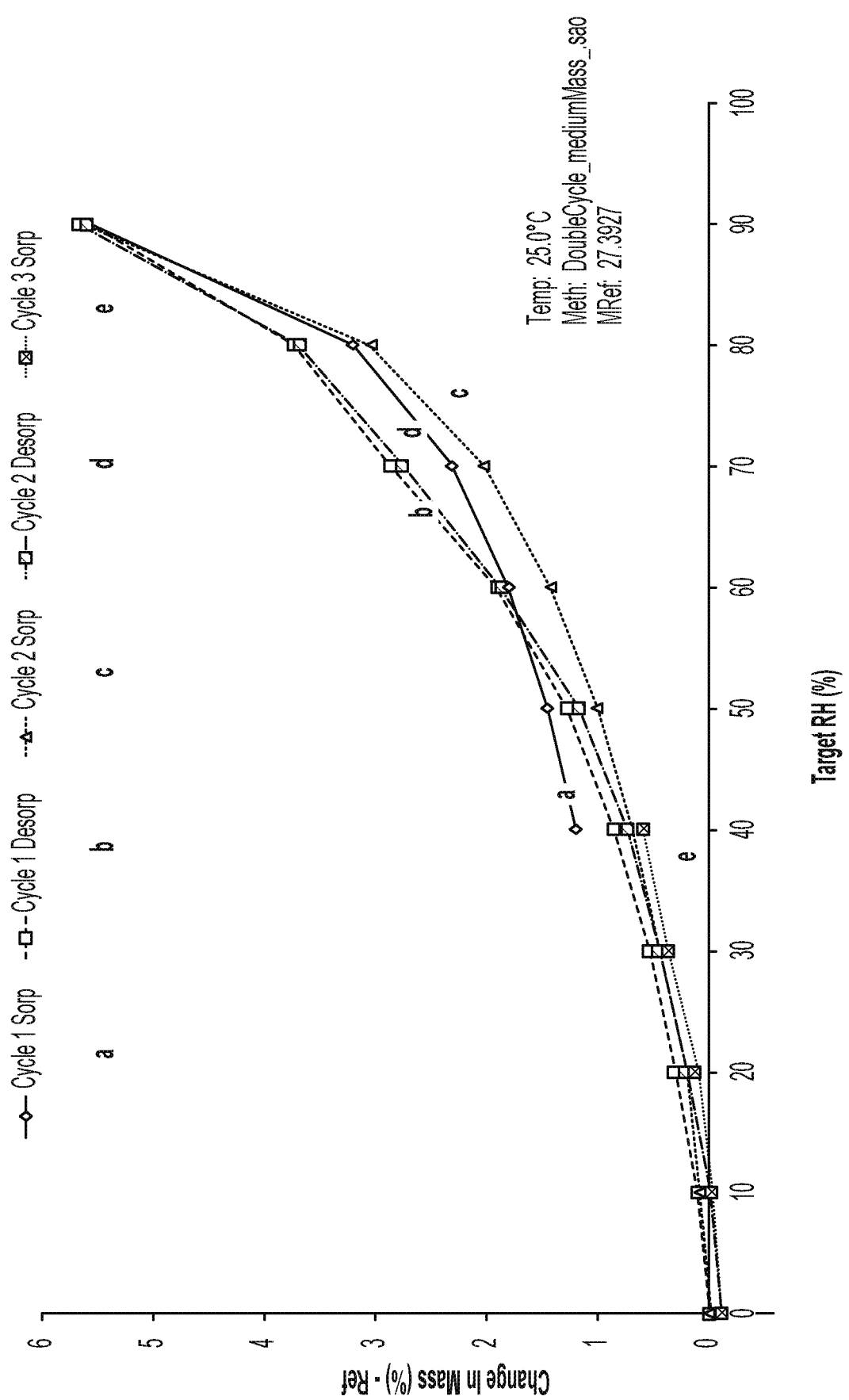
FIG. 6 is a Gravimetric Vapor Sorption (GVS)/Dynamic Vapor Sorption (DVS) isotherm plot for Compound 1, in accordance with various embodiments.

Gravimetric Vapor Sorption (GVS) shows an uptake of 6% between 0% and 90% RH. The sample is hygroscopic. The GVS isotherm plot is provided in FIG. 6.

Figure 7:
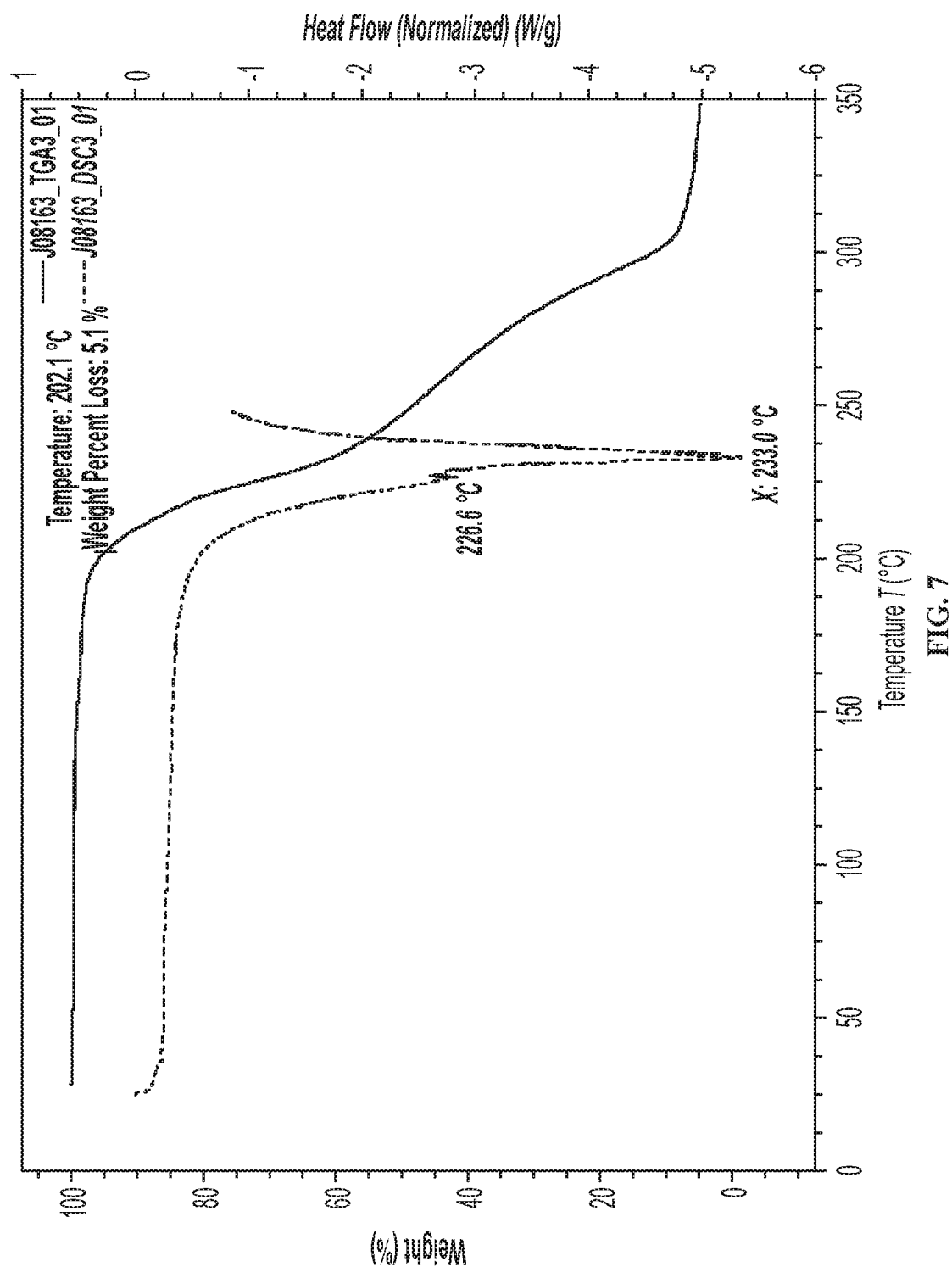
FIG. 7 is a combined Differential Scanning calorimetry (DSC)/Thermogravimetric Analysis (TGA) trace for Compound 1, in accordance with various embodiments.

The combined DSC/TGA results for (R)-2-(2-hydroxyphenylamino)-5,5-dimethyl-4,5-dihydrothiazole-4-carboxylic acid mono-hydrochloride is provided in FIG. 7. The DSC shows a split endotherm between 200° C. and 250° C. and the TGA shows that decomposition (total 5% mass loss) starts at ~202° C. An amorphous form of Compound 1 can be made by, for example, lyophilizing crystalline Compound 1 as described in Example 4 herein.

Impurities in Compound 1

Figure 8:
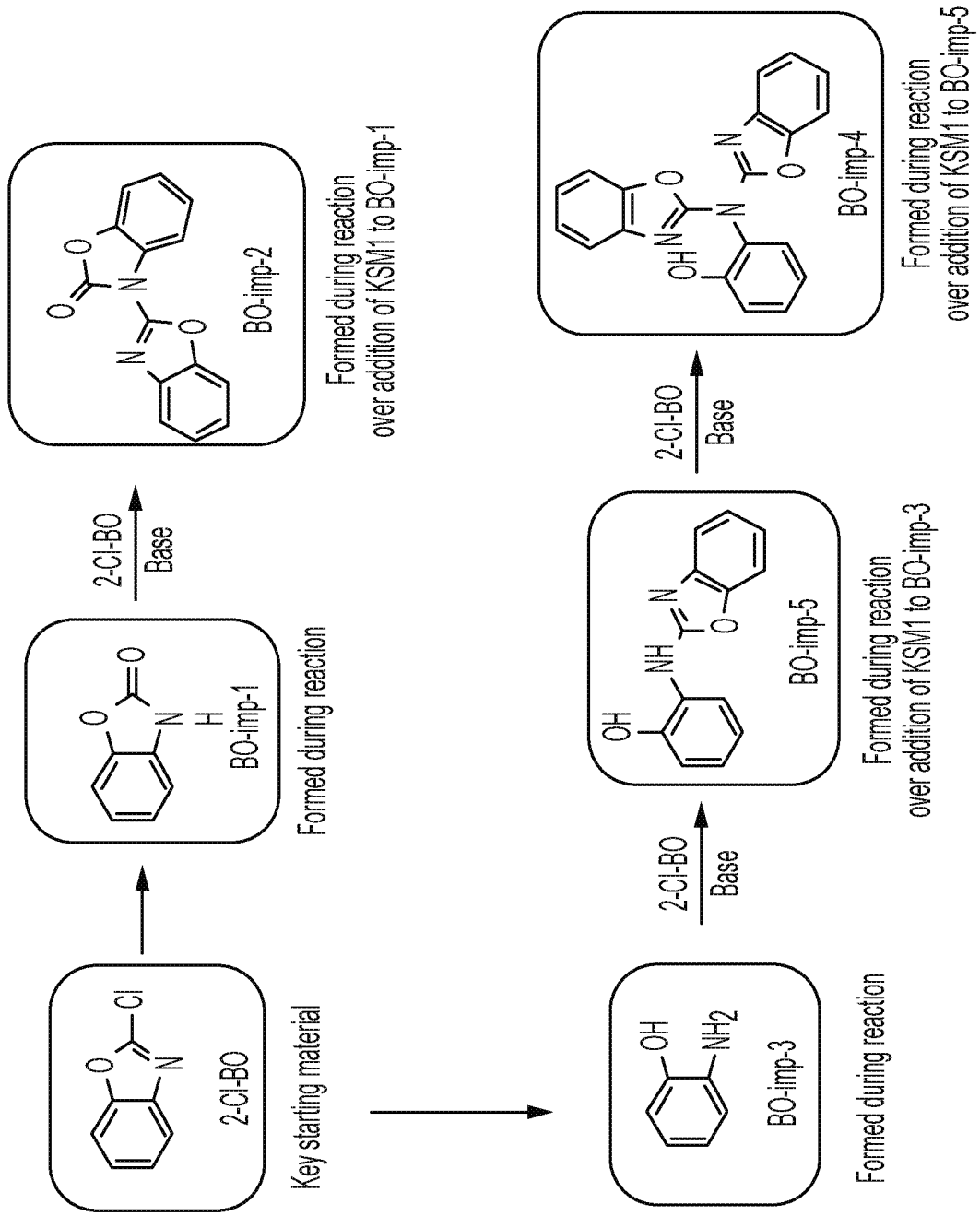
FIG. 8 is a listing of structures of impurities potentially formed during the manufacture of Compound 1, in accordance with various embodiments.
Figure 9:
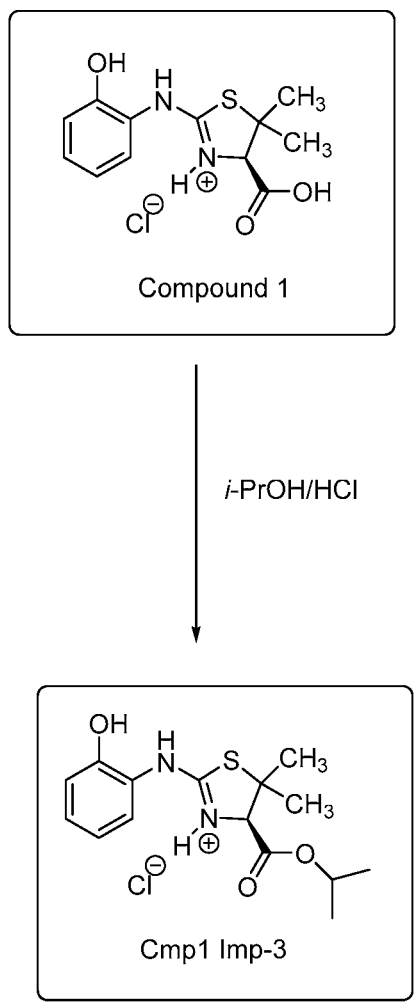
FIG. 9 illustrates the manner of forming impurity Cmp1 Imp-3, which is potentially formed during the manufacture of Compound 1, in accordance with various embodiments.

In various embodiments, Compound 1 described herein can include up to about 0.30% w/w of one or more impurities set forth in Table 5 below, and as shown in FIG. 8 and FIG. 9.

TABLE 5

| Abbreviation | Chemical Name | Structure |
|---|---|---|
| 2-Cl-BO | 2-Chlorobenzoxazole | 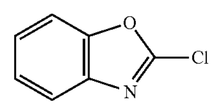 |
| L-Penicillamine | L-Penicillamine | 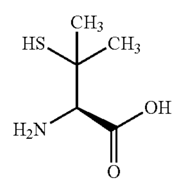 |
| BO-Imp-1 | 2-Hydroxybenzoxazole | 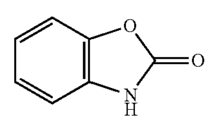 |
| BO-Imp-2 | 2'H-[2,3'-bi-1,3-benzoxazol]-2'-one | 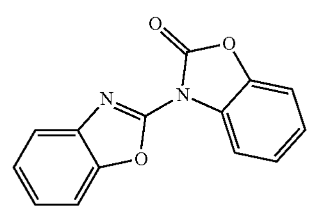 [SMILES: O=c1oc2ccccc2n1-c1nc2ccccc2o1] |
| BO-Imp-3 | 2-Aminophenol | 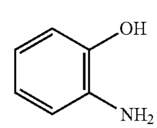 |

TABLE 5-continued

Impurities in Compound 1

| Abbreviation | Chemical Name | Structure |
|---|---|---|
| BO-Imp-4 | 2-[Bis(1,3-benzoxazol-2-yl)amino]phenol | 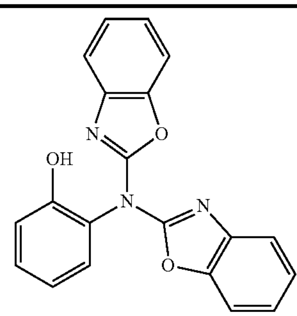 |
| BO-Imp-5 | 2-[(1,3-Benzoxazol-2-yl)amino]phenol | 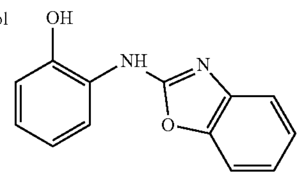 |
| Cmp1 Imp-3 | Propan-2-yl (4R)-2-(2-hydroxyanilino)-5,5-dimethyl-4,5-dihydro-1,3-thiazole-4-carboxylate | |

In various embodiments, Compound 1 has less than about 0.30% w/w, 0.25% w/w, 0.20% w/w, or 0.15% w/w of at least one impurity selected from the group consisting of 2-Cl-BO, BO-Imp-1, BO-Imp-2, BO-Imp-3, BO-Imp-4, BO-Imp-5, and Cmp1 Imp-3. In various embodiments, Compound 1 has about 0.0001% to about 0.30% w/w, about 0.0001% to about 0.25% w/w, about 0.0001% to about 0.20% w/w, about 0.001% to about 0.15% w/w, or about 0.01% to about 0.15% w/w of at least one impurity selected from the group consisting of 2-Cl-BO, BO-Imp-1, BO-Imp-2, BO-Imp-3, BO-Imp-4, BO-Imp-5, and Cmp1 Imp-3.

In various embodiments, Compound 1 has about 0.0005%, 0.001%, 0.002%, 0.003%, 0.004%, 0.005%, 0.006%, 0.007%, 0.008%, 0.009%, 0.010%, 0.012%, 0.014%, 0.016%, 0.018%, 0.020%, 0.022%, 0.024%, 0.026%, 0.028%, 0.030%, 0.032%, 0.034%, 0.036%, 0.038%, 0.040%, 0.042%, 0.044%, 0.046%, 0.048%, or 0.050% w/w of at least one impurity selected from the group consisting of 2-Cl-BO, BO-Imp-1, BO-Imp-2, BO-Imp-3, BO-Imp-4, BO-Imp-5, and Cmp1 Imp-3. In various embodiments, Compound 1 includes about 0.010% to about 0.020% w/w of impurity BO-Imp-1 and about 0.002% to about 0.004% w/w of impurity BO-Imp-5. In various embodiments, one or more of the impurities in Compound 1 described herein are present in isolated Compound 1 in the amounts described herein. In various embodiments, one or more of the impurities in Compound 1 described herein are present in isolated and purified Compound 1 in the amounts described herein. A purified Compound 1 is a quantity of Compound 1 that was subjected to one or more of any of the analytical purification techniques described herein, or other purification techniques known in the art.

Impurities BO-Imp-1 through BO-Imp-5 can arise from the 2-chlorobenzoxazole starting material. A flow chart showing the formation of these impurities is provided in FIG. 8.

BO-Imp-3 is a process impurity which forms by hydrolysis of 2-chlorobenzoxazole by a minor competitive reaction pathway with sodium hydroxide. It can be purged by filtration of the zwitterion of Compound 1. BO-Imp-3 can form as a minor impurity (0.3%) during forced degradation testing of Compound 1, such with 5N sodium hydroxide heating for 5 h.

Cmp1 Imp-3 is a process impurity that forms via acid catalyzed esterification of salt-free Compound 1 with iso-propanol solvent during the hydrochloride salt formation. Its formation can be minimized by using stoichiometric hydrogen chloride in iso-propanol, which is added to a pre-cooled suspension of the zwitterion of Compound 1 in iso-propanol. It can be purged by filtration of Compound 1. Cmp1 Imp-3 is formed as shown in FIG. 9.

The enantiomer of Compound 1 is (S)-2-(2-hydroxyphenylamino)-5,5-dimethyl-4,5-dihydrothiazole-4-carboxylic acid mono-hydrochloride, and can be designated (9-Compound 1. In various embodiments, the enantiomeric purity of Compound 1 can be at least about 95%, 97%, 98%, 99%, 99.2%, 99.4%, 99.6%, 98.8%, 99.9%, 99.99%, or more. Thus, for example, if the enantiomeric purity of Compound 1 is 99.5%, the composition contains 99.5% Compound 1 and 0.5% (9-Compound 1. The enantiomeric purity refers only to the relative amounts of Compound 1 and (9-Compound 1, and additional impurities may be present as described herein.

Compositions

The invention includes a pharmaceutical composition comprising at least one compound of the invention and at least one pharmaceutically acceptable carrier. In certain embodiments, the composition is formulated for an administration route such as oral or parenteral, for example, transdermal, transmucosal (e.g., sublingual, lingual, (trans) buccal, (trans)urethral, vaginal (e.g., trans- and perivaginally), (intra)nasal and (trans)rectal, intravesical, intrapulmonary, intraduodenal, intragastrical, intrathecal, subcutaneous, intramuscular, intradermal, intra-arterial, intravenous, intrabronchial, inhalation, and topical administration.

In various embodiments, a pharmaceutical composition of Compound 1 includes

Formula I (Compound 1)

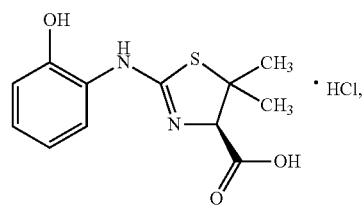

which comprises about 0.0001% to about 0.30% w/w of at least one impurity selected from the group consisting of 2-Cl-BO, BO-Imp-1, BO-Imp-2, BO-Imp-3, BO-Imp-4, BO-Imp-5, and Cmp1 Imp-3. The pharmaceutical composition can also include at least one pharmaceutically acceptable carrier, as described herein.

EXAMPLES

Various embodiments of the present invention can be better understood by reference to the following Examples which are offered by way of illustration. The present invention is not limited to the Examples given herein.

Example 1: Preparation of Compound 1 Zwitterion

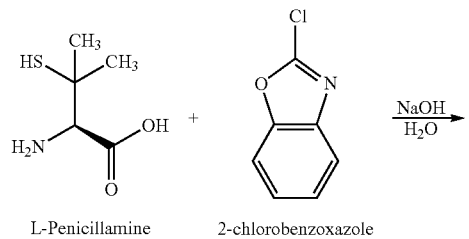

L-Penicillamine       2-chlorobenzoxazole

-continued

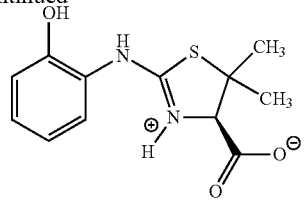

Compound 1 Zwitterion

Purified water (8 volumes) was degassed with argon for approximately 30 minutes. L-penicillamine (1.6756 mol) was added and stirred for approximately 10 minutes maintaining the temperature below 30° C. The mixture was cooled to 10±5° C. A cooled solution of sodium hydroxide (3.3512 mol) in degassed water (2 volumes) was added slowly to the above mass while maintaining temperature below 20° C., followed by slow addition of 2-chlorobenzoxazole (1.8431 mol) below 30° C. After complete addition the reaction mass was allowed to reach ambient temperature and was stirred for not less than 8 h at ambient temperature. Upon completion of the reaction, the reaction mixture was cooled to 10±5° C., diluted with iso-propyl alcohol (10 volumes) and acidified to pH 4.3-4.6 by dropwise addition of 2N aqueous hydrochloric acid below 30° C. The solution was stirred for approximately 16 h at below 5±5° C. The solid was isolated by filtration, washed with iso-propyl alcohol (3 volumes), and dried to get the zwitterion as white solid (302 g, 67.7%).

Example 2: Preparation of Compound 1 from Compound 1 Zwitterion

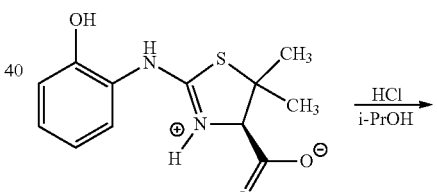

Compound 1 Zwitterion

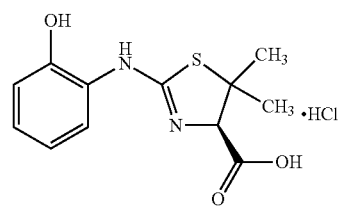

Compound 1

The zwitterion was added to iso-propyl alcohol (17.5 volumes) and cooled to 5±5° C. Freshly prepared 2M HCl in iso-propyl alcohol (1.05 equivalents with regard to zwitterion) was added below 10° C. The mixture was stirred for approximately 15 min, and the clear solution filtered under inert atmosphere. The filtrate was stirred not less than 16 h at 5±5° C. The mixture was concentrated to approximately 3 volumes below 30° C., methyl tert-butyl ether (MTBE) was added (5 volumes) and kept at 5±5° C. for not less than 20 h. The solid formed was isolated by filtration and washed Example 3: Alternative Synthesis of (R)-2-((2-hydroxyphenyl)amino)-5,5-dimethyl-4,5-dihydrothiazole-4-carboxylic acid des-HCl Compound 1 (i.e. lacking the HCl addition salt of Compound 1) can be prepared according to Scheme 4:

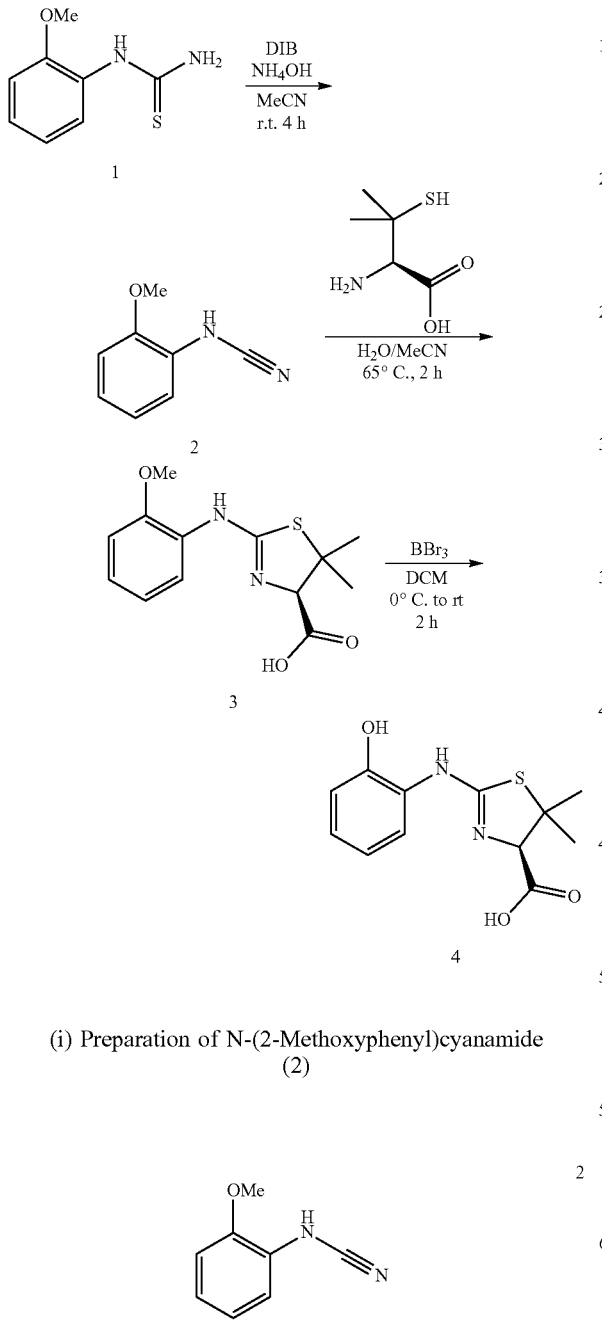

(i) Preparation of N-(2-Methoxyphenyl)cyanamide (2)

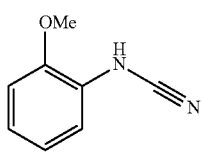

Aqueous ammonia (25%, 90 mL) was added to a stirred and ice-cooled suspension of 1-(2-methoxyphenyl)thiourea (1) (5.00 g, 27.44 mmol) in acetonitrile (90 mL). Diacetoxyiodobenzene (10.60 g, 32.92 mmol) was added portion-wise over a period of 10 min. The reaction mixture was stirred at room temperature for 4 h, and the precipitated sulfur was filtered. The filtrate was concentrated to approximately 50% of its initial volume and extracted with ethyl acetate (3×20 mL). The ethyl acetate layer was washed with water (2×30 mL) and then with brine (50 mL). The organic layer was dried over anhydrous solid $Na_2SO_4$, filtered and the filtrate concentrated under reduced pressure. The resultant residue was purified by flash column chromatography using petroleum ether/ethyl ether (1:1) to give the N-(2-methoxyphenyl)-cyanamide (2) (3.33 g, 82% yield). 300 MHz $^1$H-NMR ($CDCl_3$, ppm): 7.08 (ddd, J=7.5, 1.9, 0.5 Hz, 1H) 7.04 (ddd, J=7.5, 7.5, 1.9 Hz) 6.98 (ddd, J=7.5, 7.5, 1.7 Hz) 6.88 (dd, J=7.5, 1.7 Hz) 6.26 (s, 1H) 3.88 (s, 3H). ESI-MS (m/z): 149 $[M+H]^+$.

(ii) Preparation of ((R)-2-((2-methoxyphenyl)amino)-5,5-dimethyl-4,5-dihydrothiazole-4-carboxylic acid (3)

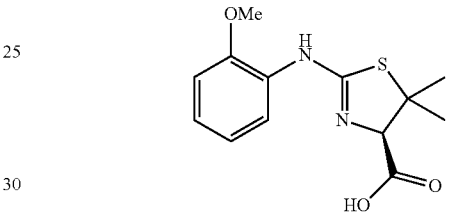

A mixture N-(2-methoxyphenyl)cyanamide (2) (1.00 g, 6.75 mmol) and L-penicillamine (1.21 g, 8.10 mmol) in deionized water/acetonitrile (20 mL/20 mL) was heated at reflux under an argon atmosphere for 2 h. The mixture was then concentrated under reduced pressure, and residue purified by reverse phase chromatography to afford (R)-2-((2-methoxyphenyl)amino)-5,5-dimethyl-4,5-dihydrothiazole-4-carboxylic acid (3) (0.92 g, 49% yield). 300 MHz $^1$H-NMR ($CD_3OD$, ppm): 7.43-7.33 (m, 2H) 7.15 (dd, J=8.3, 1.1 Hz, 1H) 7.03 (ddd, J=7.7, 7.7, 1.2 Hz) 4.42 (s, 1H) 3.91 (s, 3H) 1.77 (s, 3H) 1.60 (s, 3H). ESI-MS (m/z): 281 $[M+H]^+$.

(iii) Preparation of (R)-2-((2-hydroxyphenyl)amino)-5,5-dimethyl-4,5-dihydrothiazole-4-carboxylic acid (4)

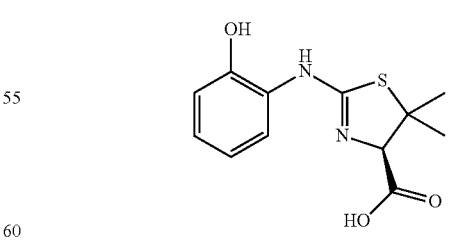

Boron tribromide ($BBr_3$) (2.19 mL, 12.84 mmol) was added to a solution of ((R)-2-((2-methoxyphenyl)amino)-5,5-dimethyl-4,5-dihydrothiazole-4-carboxylic acid (3) (360 mg, 1.28 mmol) in $CH_2Cl_2$ (20 mL) at 0° C. The reaction mixture was stirred at ambient temperature for 3 h, then water (2 mL) was added and the resulting suspension was stirred for 10 min. The resultant precipitate was filtered and removed. The filtrate was evaporated and purified by reverse phase chromatography to afford (R)-2-((2-hydroxyphenyl)amino)-5,5-dimethyl-4,5-dihydrothiazole-4-carboxylic acid (4) (210 mg, 64% yield). 300 MHz $^1$H-NMR (CD$_3$OD, ppm): 6.94-6.86 (m, 2H) 6.82-6.77 (m, 1H) 6.73 (ddd, J=7.5, 7.5, 1.5 Hz) 4.19 (s, 1H) 3.91-1.68 (s, 3H) 1.49 (s, 3H). ESI-MS (m/z): 267 [M+H]$^+$.

Example 4: Amorphous Compound 1

Figure 10:
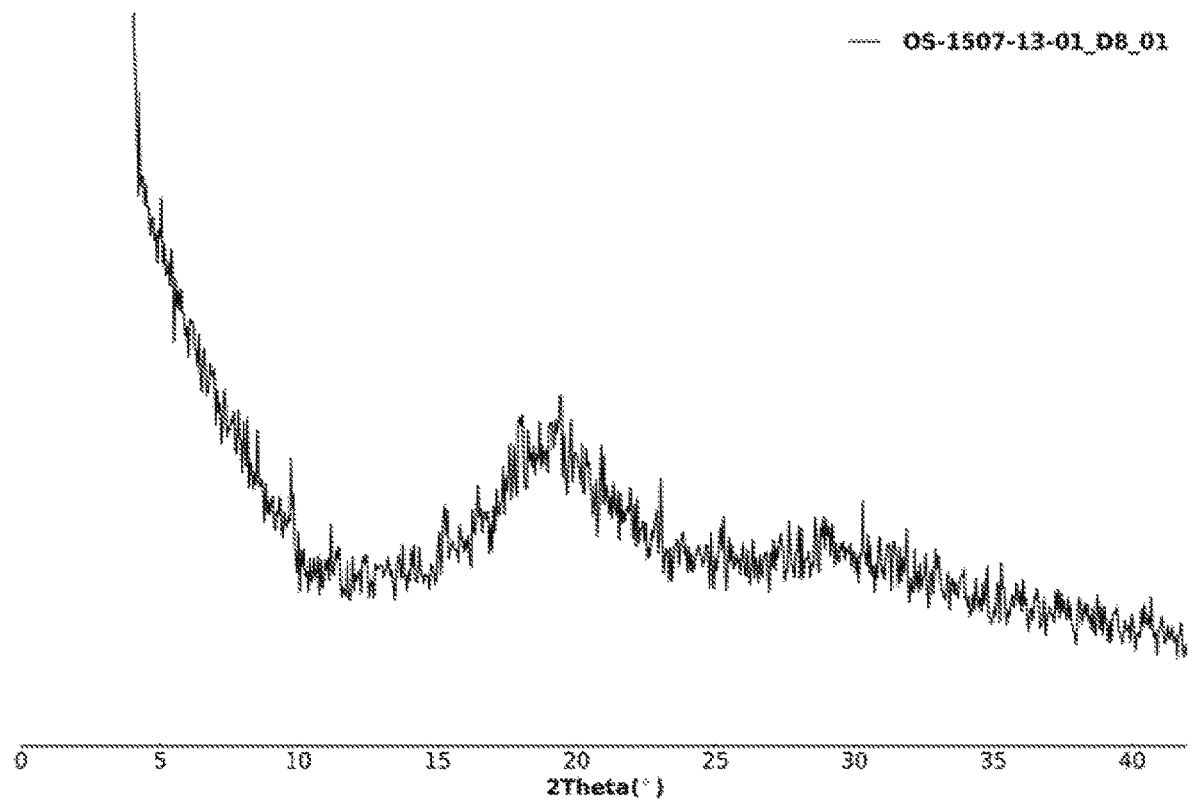
FIG. 10 illustrates an XPRD spectrum of amorphous Compound 1.

An amorphous form of Compound 1 can also be prepared as follows:
(R)-2-(2-hydroxyphenylamino)-5,5-dimethyl-4,5-dihydrothiazole-4-carboxylic acid mono-hydrochloride (Compound 1, 200 mg) was dissolved in a tert-butanol:water mixture (1:1 ratio, 40 vol., 8 ml) at RT. The solution was filtered to remove potential seeds, and the filtered solution was frozen in a round bottom flask over a bath of dry ice and acetone. The sample was then set for freeze-drying. The XPRD of the recovered solid after freeze-drying, which is amorphous Compound 1, is shown in FIG. 10.

Example 5: Analytical Testing of Batches of Compound 1

Starting materials for the preparation of Compound 1 are commercially available and are tested to ensure that acceptance criteria are met prior to use. The specifications for starting materials (L)-penicillamine and 2-chlorobenzoxazole are provided in Table 6.

TABLE 6

| Starting Material Specifications | |
|---|---|
| (L)-Penicillamine Release Specifications | |

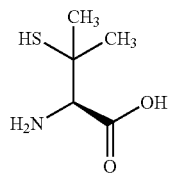

| Test Attribute | Release Specification |
|---|---|
| Appearance | Off-white to white solid |
| Identification by $^1$H-NMR, IR, and Mass Spectroscopy | Complies with the structure |
| Chromatographic Purity by HPLC (ELSD) | NLT$^a$ 98.5% |
| Total Impurities | NMT$^b$ 1.5% |
| Dimer | NMT 1.0% |
| Chiral Purity by HPLC | NLT 99.0% |
| Loss on Drying | NMT 1.0% |

| 2-Chlorobenzoxazole Release Specifications | |
|---|---|

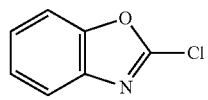

| Test Attribute | Release Specification |
|---|---|
| Appearance | Colorless to pale yellow liquid |
| Identification by $^1$H-NMR | Complies with structure |
| Purity (area %) by GC | NLT$^a$ 98.0% |
| BO-Imp-1 | NMT$^b$ 1.0% |

$^a$NLT = not less than
$^b$NMT = not more than

Batches of Compound 1 suitable for administration to individuals and prepared according to the method describe herein were analyzed for purity.

TABLE 7

In-Process Testing for Compound 1
Step 1: Preparation of Compound 1 Zwitterion

| Step | Test | Method | Action Limit |
|---|---|---|---|
| After Initial Reaction | % L-Penicillamine | HPLC ELSD | NMT$^a$ 1.0% |
| After Initial Drying | Water Content | Karl Fischer | NMT 1.0% |
| | Purity and Related Substances of Zwitterion | HPLC UV | Zwitterion: NLT$^b$ 98.5% 2-Cl BO: NMT 0.15% BO-Imp-1: NMT 0.15% BO-Imp-2: NMT 0.15% BO-Imp-3: NMT 0.15% BO-Imp-4: NMT 0.15% BO-Imp-5: NMT 0.15% Cmpd 1-Imp-3: NMT 0.5% |
| | % L-Penicillamine | HPLC ELSD | NMT 0.3% |
| | Chiral Impurity | HPLC UV | NMT 1.0% |
| | Benzene | GC | NMT 2 ppm |
| | Triethylamine | GC-MS | NMT 320 ppm |
| After Final Drying | Loss on Drying | USP <731> | Report result |
| | Residue on Ignition | USP <281> | Report result |

Step 2: Preparation of Compound 1

| Step | Test | Method | Action Limit |
|---|---|---|---|
| Iso-propyl Alcohol/HCl | Molarity | Titration | Report result |
| After Initial Reaction | Purity and Related Substances | HPLC UV | Purity: NLT 98.5% 2-Cl BO: NMT 0.15% BO-Imp-1: NMT 0.15% BO-Imp-2: NMT 0.15% BO-Imp-3: NMT 0.15% BO-Imp-4: NMT 0.15% BO-Imp-5: NMT 0.15% Compound 1-Imp-3: NMT 0.5% Unspecified Impurities: NMT 0.15% |
| | Chiral Impurity | HPLC UV | NMT 1.0% |
| | % L-Penicillamine | HPLC ELSD | NMT 0.5% |
| | Residue on Ignition | ROI | Report results |
| After Purification | Residue on Ignition | ROI | NMT 0.25% |
| After Drying | Residual Solvents | GC | Ethanol: NMT 5,000 ppm; n-Butanol: NMT 5,000 ppm; Iso-propyl alcohol: NMT 5,000 ppm; Methyl tert-butyl ether: NMT 5,000 ppm; Chloroform: NMT 60 ppm; 1,2-Dichloroethane: NMT 5 ppm |
| | Water | Karl Fischer | NMT 1.0% |

$^a$NMT = not more than
$^b$NLT = not less than

Example 6: Analytical Methods Used in Testing Compound 1

Analytical methods, in various embodiments, were carried out with equipment and parameters set forth below. The testing was conducted on batches Compound 1 suitable for administration to individuals according to the methods and specifications belonging to the USP (United States Pharmacopeia).

TABLE 8

Analytical Procedures For Compound 1

| Test | Summary of the Analytical Procedure | | | |
|---|---|---|---|---|
| Description | Visual Examination | | | |
| IR Identification | FT-IR | | | |
| HPLC Method 1 Identification, Purity, Assay, and Impurities BO-Imp-1, BO-Imp-4, BO-Imp-5, Compound 1 Imp-3, Individual Unspecified Impurities, Total Impurities | Identification is confirmed by verifying the retention time of the Compound 1 peak in the drug substance is consistent with that of the working standard. Purity, assay, and related substances are performed using reversed-phase HPLC and the following chromatographic conditions. | | | |
| | Instrument | Suitable HPLC with variable wavelength UV detector | | |
| | Column | X-Bridge C18, 250 × 4.6 mm, 5 µm | | |
| | Mobile Phase A | 25 mM $K_2HPO_4$ in water, pH 8.4: Methanol (95:5) | | |
| | Mobile Phase B | Acetonitrile: Methanol (50:50) | | |
| | Gradient | Time | % Mobile Phase A | % Mobile |
| | | 0.01 | 75 | 25 |
| | | 2.00 | 75 | 25 |
| | | 12.00 | 55 | 45 |
| | | 18.00 | 55 | 45 |
| | | 35.00 | 35 | 65 |
| | | 40.00 | 35 | 65 |
| | | 40.10 | 75 | 25 |
| | | 50.00 | 75 | 25 |
| | Flow Rate | 1.0 mL/min | | |
| | Injection Volume | 8.0 µL | | |
| | Wavelength | 225 nm | | |
| | Column Temperatur | 30° C. | | |
| | Detector Cell | 40° C. | | |
| | Run Time | 50 minutes | | |
| HPLC Method Limit Test 2-Cl-BO and BO-Imp-2 | A limit test is performed for process impurities 2-Cl-BO and BO-Imp-2 are performed using reversed-phase HPLC and the following chromatographic conditions. | | | |
| | Instrument | Suitable HPLC with variable wavelength UV detector | | |
| | Column | X-Bridge C18, 250 × 4.6 mm, 5 µm | | |
| | Mobile Phase A | 25 mM $K_2HPO_4$ in water, pH 8.4: Methanol (95:5) | | |
| | Mobile Phase B | Acetonitrile: Methanol (50:50) | | |
| | Gradient | Time | % Mobile Phase A | % Mobile |
| | | 0.01 | 75 | 25 |
| | | 2 | 75 | 25 |
| | | 12 | 55 | 45 |
| | | 18 | 55 | 45 |
| | | 35 | 35 | 65 |
| | | 40 | 35 | 65 |
| | | 40.1 | 75 | 25 |
| | | 50 | 75 | 25 |
| | Flow Rate | 1.0 mL/min | | |
| | Injection Volume | 10.0 µL | | |
| | Wavelength | 250 nm | | |
| | Column Temperatur | 30° C. | | |
| | Detector Cell | 40° C. | | |
| | Run Time | 50 minutes | | |

TABLE 8-continued

Analytical Procedures For Compound 1

| Test | Summary of the Analytical Procedure | | | |
|---|---|---|---|---|
| HPLC Method 3 BO-Imp-3 | A limit test for BO-Imp-3 is performed using reversed-phase HPLC and the following chromatographic conditions. | | | |
| | Instrument | Suitable HPLC with variable wavelength UV detector | | |
| | Column | Waters X-Bridge C18, 250 × 4.6 mm, 5 μm | | |
| | Mobile Phase A | 25 mM $K_2HPO_4$ in water, pH 8.4: methanol (95:5) | | |
| | Mobile Phase B | Acetonitrile: Methanol (50:50) | | |
| | Gradient | Time | % Mobile | % Mobile |
| | | 0.01 | 75 | 25 |
| | | 2 | 75 | 25 |
| | | 12 | 55 | 45 |
| | | 18 | 55 | 45 |
| | | 35 | 35 | 65 |
| | | 40 | 35 | 65 |
| | | 40.1 | 75 | 25 |
| | | 50 | 75 | 25 |
| | Flow Rate | 1.0 mL/min | | |
| | Injection Volume | 10 μL | | |
| | Wavelength | 225 nm | | |
| | Column Temperatur | 30° C. | | |
| | Autosampler | 15° C. | | |
| | Detector Cell | 40° C. | | |
| | Run Time | 50 minutes | | |
| HPLC Method 4 (L)-Penicillamine | A limit test for L-penicillamine is performed using reversed-phase HPLC using a MS detector and the following chromatographic conditions. | | | |
| HPLC Method 5 S-Compound 1 Imp-3 | Gradient | Time | % Mobile | % Mobile |
| | | 0.0 | 100 | 0 |
| | | 10 | 20 | 80 |
| | | 16 | 20 | 80 |
| | | 17 | 100 | 0 |
| | | 22 | 100 | 0 |
| | Flow Rate | 0.5 mL/min | | |
| | Injection Volume | 10 μL | | |
| | Wavelength | 254 nm | | |
| | Column Temperature | 35° C. | | |
| | Run Time | 22 minutes | | |
| | Mass Parameters | | | |
| | Nebulizer Pressure | 40 psi | | |
| | Dry Gas Flow Rate | 10 L/min | | |
| | Fragmentor Voltage | 70 V | | |
| | Capillary Voltage | 3,000 V | | |
| | Dry Gas Temperature | 350° C. | | |
| | Collection Mode | SIM mode: positive signal for 150 ion | | |
| | A limit test for BO-Imp-3 is performed using chiral HPLC and the following chromatographic conditions. | | | |
| | Instrument | Suitable HPLC with variable wavelength UV detector | | |
| | Column | Chiralpak IG, 250 × 4.6 mm, 5 μm | | |
| | Mobile Phase: | 0.1% diethylamine in acetonitrile: methanol 95:5 | | |
| | Flow Rate | 0.8 mL/min | | |
| | Injection Volume | 10 μL | | |
| | Wavelength | 285 nm | | |
| | Column Temperature | 25° C. | | |
| | Autosampler Temperature | 25° C. | | |
| | Detector Cell Temperature | 40° C. | | |
| | Run Time | 70 minutes | | |

TABLE 8-continued

Analytical Procedures For Compound 1

| Test | Summary of the Analytical Procedure | | | |
|---|---|---|---|---|
| HPLC Method 6 Chiral Purity | Quantitation of (S)-Compound 1 is performed using chiral HPLC chromatography and the following chromatographic conditions. | | | |
| | Instrument | Suitable HPLC with variable wavelength detector | | |
| | Column | Chiralcel OX-3, 250 × 4.6 mm, 3 μm | | |
| | Mobile Phase A | 0.3% trifluoroacetic acid in n-hexane | | |
| | Mobile Phase B | 0.1% diethylamine in ethanol: iso-propyl alcohol 8:2 | | |
| | Gradient | Time | % Mobile Phase A | % Mobile Phase B |
| | | 0.01 | 80 | 20 |
| | | 15.0 | 80 | 20 |
| | Flow Rate | 1.0 mL/min | | |
| | Injection Volume | 10 μL | | |
| | Wavelength | 285 nm | | |
| | Column Temperature | 25° C. | | |
| | Detector Cell Temperature | 40° C. | | |
| | Run Time | 15 minutes | | |
| Residual Solvents Ethanol, Iso-propyl Alcohol, n-Butanol, MTBE [a] | Quantitation of ethanol, iso-propyl alcohol, n-butanol, and methyl tert-butyl ether is performed using a headspace GC method and flame ionization detection. The chromatographic conditions are listed below. | | | |
| | Instrument | Suitable GC with flame ionization detector (FID) | | |
| | Column | DB-1, 60 m × 0.32 mm, 3 μm | | |
| | Carrier Gas | Helium | | |
| | Temperature Program | Rate (° C./min) | Temperature (° C.) | Hold Time (Minutes) |
| | | — | 50 | 2 |
| | | 3 | 80 | 5 |
| | | 15 | 260 | 11 |
| | Flow Rate | 1.5 mL/min | | |
| | Injection Mode | Split | | |
| | Split Ratio | 10:1 | | |
| | Detector Temperature | 280° C. | | |
| | Make-Up Gas | Helium | | |
| | Make-Up Flow | 30.0 mL/min | | |
| | $H_2$ Flow | 40.0 mL/min | | |
| | Air Flow | 400.0 mL/min | | |
| | Run Time | 40.0 minutes | | |
| Residual Solvent Chloroform | Quantitation of chloroform is performed using a GC method and electron impact mass detection. The chromatographic conditions are listed below. | | | |
| | Instrument | Suitable GC with electron impact mass detection | | |
| | Column | DB-1, 60 m × 0.32 mm, 3 μm | | |
| | Carrier Gas | Helium | | |
| | Oven Temperature | 50° C., hold at ° C. for 2 minutes | | |
| | Temperature Ramp | 50° C. to 80° C. at 3° C./min, hold at 80° C. for 7 minutes 80° C. to 260° C. at 50° C./min, hold at 260° C. for 12 minutes | | |
| | Flow Rate | 1.0 mL/min | | |
| | Injection Mode | Split | | |
| | Split Ratio | 10:1 | | |
| | Injector Temperature | 200° C. | | |
| | Injection Volume | 2 μL | | |
| | Make-Up Flow | 30.0 mL/min | | |
| | Run Time | 34.6 minutes | | |
| Residual Solvent 1,2-Dichloroethane | Quantitation of 1,2-Dichloroethane is performed using a GC method and electron impact mass detection. The chromatographic conditions are listed below. | | | |
| | Instrument | Suitable GC with electron impact mass detection | | |
| | Column | DB-624, 30 m × 0.32 mm, 1.8 μm | | |
| | Carrier Gas | Helium | | |
| | Oven Temperature | 40° C., hold at 40° C. for 5 minutes | | |
| | Temperature Ramp | 40° C. to 60° C. at 4° C./min, hold at 60° C. for 1 minute 60° C. to 250° C. at 50° C./min, hold at 250° C. for 6 minutes | | |
| | Flow Rate | 1.5 mL/min | | |
| | Injection Mode | Split | | |
| | Split Ratio | 5:1 | | |
| | Injector Temperature | 220° C. | | |
| | Injection Volume | 1 μL | | |
| | Run Time | 20.8 minutes | | |

TABLE 8-continued

Analytical Procedures For Compound 1

| Test | Summary of the Analytical Procedure |
|---|---|
| Water | USP <921>, Method Ia |
| Residue on Ignition | USP <281> |
| Elemental Impurities Arsenic, Cadmium, Mercury, Lead, Cobalt, Vanadium, and Nickel | Arsenic (As), cadmium (Cd), mercury (Hg), lead (Pb), cobalt (Co), vanadium (V), and nickel (Ni) content are determined using Inductively Coupled Plasma (ICP) with mass spectral detection. |
| Elemental Impurities Lithium, | Lithium (Li), antimony (Sb), and copper (Cu), content are determined using ICP with Optical Emission Spectroscopy (OES) detection. |
| Powder XRD | USP <941> |
| Microbial Analysis | USP <61>, USP <62> |

In various embodiments, the methods described herein produce Compound 1 with one or more of the parameters, such amounts of impurities, set forth in Table 9:

TABLE 9

Compound 1 Specifications

| Parameter | Test Method | Specification (Acceptance Criteria Applied) |
|---|---|---|
| Description | Visual Examination | White to off-white solid |
| Identification | | |
| IR | FT-IR | Conforms to structure |
| HPLC | HPLC Method 1 | The retention time of the principal peak in the sample chromatogram corresponds to that of the standard chromatogram |
| Chloride | USP <191> Test A | With Silver Nitrate TS, solution of chlorides yield a white, curdy precipitate that is insoluble in nitric acid but is soluble in a slight excess of 6N ammonium hydroxide |
| Purity | HPLC Method 1 | NLT$^a$ 98.5% (% area) |
| Assay | HPLC Method 1 | 97.0%-103.0% |
| Impurities | | |
| 2-Cl-BO | HPLC Method 2 | NMT 0.004% |
| BO-Imp-1 | HPLC Method 1 | NMT 0.15% |
| BO-Imp-2 | HPLC Method 2 | NMT 0.004% |
| BO-Imp-3 (2-aminophenol) | HPLC Method 3 | NMT 0.004% |
| BO-Imp-4 | HPLC Method 1 | NMT 0.15% |
| BO-Imp-5 | | NMT 0.15% |
| Compound 1 Imp-3 | | NMT 0.5% |
| L-Penicillamine | HPLC Method 4 | NMT 0.004% |
| S-Compound 1 Imp-3 | HPLC Method 5 | NMT 0.15% |
| Chiral Purity | HPLC Method 6 | NMT$^b$ 0.5% S-Isomer |
| Any Individual Unspecified Impurity | HPLC Method 1 | NMT 0.15% |
| Total Impurities | | NMT 1.5% |
| Residual Solvents | | |
| Ethanol | GC-HS Method 1 | NMT 5,000 ppm |
| Iso-propyl Alcohol | | NMT 5,000 ppm |
| n-Butanol | | NMT 5,000 ppm |
| Methyl tert-butyl Ether | | NMT 5,000 ppm |
| Chloroform | GC-MS Method 2 | NMT 60 ppm |
| 1,2-Dichloroethane | GC-MS Method 3 | NMT 5 ppm |
| Water | Karl Fischer | NMT 1.0% (w/w) |
| Residue on Ignition | USP <281> | NMT 0.25% w/w |
| Elemental Impurities | | |
| Arsenic | ICP-MS | NMT 1.5 ppm |
| Cadmium | | NMT 0.2 ppm |
| Mercury | | NMT 0.3 ppm |
| Lead | | NMT 0.5 ppm |
| Cobalt | | NMT 0.5 ppm |
| Vanadium | | NMT 1 ppm |
| Nickel | | NMT 2 ppm |
| Lithium | ICP-OES | NMT 55 ppm |
| Antimony | | NMT 120 ppm |
| Copper | | NMT 300 ppm |
| Powder XRD | XRPD | Crystalline |
| Microbial Analysis | | |
| TAMC | USP <61>, | NMT $10^3$ in 1 g |
| TYMC | USP <62> | NMT $10^2$ in 1 g |
| E. coli | | Absent in 1 g |

In various embodiments, Compound 1 produced according to the methods described herein has one or more of the analytical parameters, including amounts of impurities, set forth in Table 10.

TABLE 10

Data for Compound 1 Drug Substance Batches

| | | Batch Number |
|---|---|---|
| Attribute | Proposed Specifications | Drug Batch |
| Description Identification | White to off-white solid | White solid |
| $^1$H-NMR $^a$ | Conforms to structure | NT |
| LC-MS $^a$ | Conforms to m/z | NT |
| IR | IR spectrum conforms to the structure of the molecule | Complies |
| HPLC | The retention time of the principal peak in the sample chromatogram corresponds to that of the standard chromatogram | Complies |
| Chloride | With Silver Nitrate TS, solution of chlorides yields a white, curdy precipitate that is insoluble in nitric acid but is soluble in a slight excess of 6N ammonium hydroxide | Complies |
| Purity | NLT 98.5% (% area) | 99.7 |
| Assay | 97.0% 0 103.0% | 100.8 |

TABLE 10-continued

Data for Compound 1 Drug Substance Batches

| Attribute | Proposed Specifications | Batch Number Drug Batch |
|---|---|---|
| Specified Impurities | | |
| 2-Cl-BO | NMT 0.004% | <0.004 [d] |
| BO-Imp-1 | NMT 0.15% | 0.05 |
| BO-Imp-2 | NMT 0.004% | <0.004 [d] |
| BO-Imp-3 (2-aminophenol) | NMT 0.004% | <0.004 [d] |
| BO-Imp-4 | NMT 0.15% | <0.013 (LOD [e]) |
| BO-Imp-5 | NMT 0.15% | <0.045 (LOQ [f]) |
| Compound 1 Imp-3 | NMT 0.5% | 0.16 |

TABLE 11

Release Data for Compound 1 Drug Substance Batches

| Attribute | Proposed Specifications | Batch Number Drug Batch |
|---|---|---|
| L-Penicillamine | NMT 0.004% | <0.004 [d] |
| S-Compound 1 Imp-3 | NMT 0.15% | <0.15 [d] |
| Chiral Purity (S-Any Individual | NMT 0.5% NMT 0.15% | <0.030 (LOD) |
| Unspecified Impurity | | |
| RRT 1.54 | | <0.049 (LOQ) |
| RRT 1.85 | | 0.11 |
| RRT 2.49 | | <0.049 (LOQ) |
| RRT 3.27 | | ND |
| RRT 3.87 | | <0.049 (LOQ) |
| RRT 3.95 | | <0.049 (LOQ) |
| Total Impurities | NMT 1.5% | 0.3 |
| Residual Solvents | | |
| Ethanol | NMT 5,000 ppm | <150 ppm (LOD) |
| Iso-propyl Alcohol | NMT 5,000 ppm | 3,507 ppm |
| n-Butanol | NMT 5,000 ppm | <150 ppm (LOD) |
| MTBE | NMT 5,000 ppm | <150 ppm (LOD) |
| Chloroform | NMT 60 ppm | <3.6 ppm (LOD) |
| 1,2-Dichloroethane | NMT 5 ppm | <0.4 ppm (LOD) |
| Water | NMT 1.0% (w/w) | 0.18 |
| Residue on Ignition | NMT 0.25% w/w | 0.06 |
| Elemental Impurities | | |
| Arsenic | NMT 1.5 ppm | <0.225 ppm (PDL) [g] |
| Cadmium | NMT 0.2 ppm | <0.03 ppm (PDL) |
| Mercury | NMT 0.3 ppm | <0.045 ppm (PDL) |
| Lead | NMT 0.5 ppm | <0.075 ppm (PDL) |
| Cobalt | NMT 0.5 ppm | <0.15 ppm (PDL) |
| Vanadium | NMT 1 ppm | <0.075 ppm (PDL) |
| Nickel | NMT 2 ppm | <1.51 ppm |
| Lithium | NMT 55 ppm | <3 ppm |
| Antimony | NMT 120 ppm | <3 ppm |
| Copper | NMT 300 ppm | <3 ppm |
| Powder XRD | Crystalline | Crystalline |
| Microbial Analysis | | |
| TAMC | NMT 10³ cfu in 1 g | <10 |
| TYMC | NMT 10² cfu in 1 g | <10 |
| E. coli | Absent in 1 g | Absent |

[a] Testing performed for Batch A011800996 and is not required for routine release.
[b] NT = not tested
[c] ND = not detected
[d] Result obtained after development and qualification of Methods 2-5.
[e] LOD = limit of detection
[f] LOQ = limit of quantitation
[g] PDL = practical detection limit

TABLE 12

Release Data for Compound 1 Drug Substance Batch 2

| Sl. No. | Tests | Results | Limits |
|---|---|---|---|
| 1 | Appearance | White solid | White to off white solid |
| 2 | Identification | | |
| | By FT-IR | Complies | Should conform to the structure of the molecule |
| | By HPLC | Complies | The retention time of principal peak obtained in the chromatogram of sample solution should correspond to that of standard solution, as prepared under test for assay. |
| | By Chloride test | Complies | Curdy precipitate that is insoluble in nitric acid but is soluble in a slight excess of 6N ammonium hydroxide. |
| 3 | Purity and Related substances (area %) by HPLC | | |
| | Purity by HPLC (area %) | 99.9% | Not less than 98.5% |
| | 2-Cl BO | <DL (0.004%) | Not more than 0.004% |
| | BO-Imp-I | <0.013% (DL) | Not more than 0.15% |
| | BO-Imp-2 | <DL (0.004%) | Not more than 0.004% |
| | BO-Imp-3; aka 2-aminophenol | <DL (0.004%) | Not more than 0.004% |
| | BO-Imp-4 | <0.013% (DL) | Not more than 0.15% |
| | BO-Imp-5 | <0.012 (DL) | Not more than 0.15% |
| | CT-044-Imp-3 | 0.05% | Not more than 0.5% |
| | L-Penicillamine content by LC-MS | <DL (0.004%) | Not more than 0.004% |
| | S-CT-044-IMP-3 | Complies | Not more than 0.15% |
| | Unspecified impurities | | |
| | at RRT 1.84 | <0.015 (DL) | Not more than 0.15% |
| | Total impurities | 0.05% | Not more than 1.5% |
| 4 | Chiral impurity (area %) by HPLC | <0.030% (BDL) | Not more than 0.5% (S-isomer) |
| " | Assay by HPLC (% w/w) | 99.6% | 97.0 to 103.0% |
| 6 | Water content (% w/w) by KF | 0.096% | Not more than 1.0% |
| 7 | Residue on Ignition (% w/w) | 0.050% | Not more than 0.25% |
| 8 | Residual solvents by GC-HS (ppm) | | |
| | Ethanol | <150 ppm (BDL) | Not more than 5000 ppm |
| | n-butanol | <150 ppm (BDL) | Not more than 5000 ppm |
| | Isopropyl alcohol | 3036 ppm | Not more than 5000 ppm |
| | Methyl tertiary butyl ether | <151 ppm (BDL) | Not more than 5000 ppm |
| | Residual solvents by GC-MS (ppm) | | |
| | Chloroform | <3.6 ppm (BDL) | Not more than 60 ppm |
| | 1,2-Dichloroethane | <0.4 ppm (BDL) | Not more than 5 ppm |
| 9 | Elemental impurity by ICP-MS (ppm) | | |
| | Arsenic | <0.225 ppm (BDL) | Not more than 1.5 ppm |
| | Cadmium | <0.03 ppm (BDL) | Not more than 0.2 ppm |
| | Mercury | <0.045 ppm (BDL) | Not more than 0.3 ppm |
| | Lead | <0.075 ppm (BDL) | Not more than 0.5 ppm |
| | Cobalt | <0.15 ppm (BDL) | Not more than 0.5 ppm |
| | v11adium | <0.075 ppm (BDL) | Not more than 1 ppm |
| | Nickel | 2.7 ppm | Not more than 20 ppm |
| 10 | Elemental impurity by ICP-OES (ppm) | | |
| | Lithium | BDL (DL-3 ppm) | Not more than 55 ppm |
| | Antimony | BDL (DL 3 ppm) | Not more than 120 ppm |
| | Copper | BDL (DL-3 ppm) | Not more than 300 ppm |
| 11 | Powder XRD | Crystalline | Should be crystalline |

TABLE 12-continued

Release Data for Compound 1 Drug Substance Batch 2

| Sl. No. | Tests | Results | Limits |
|---|---|---|---|
| 12 | Microbial Analysis | | |
| | TAMC | <10 CFU/g | Not more than $10^3$ CFU/g |
| | TYMC | <10 CFU/g | Not more than $10^2$ CFU/g |
| | E.coli | Absent | Ab sent/g |

DL = detection limit;
BDL = below detection limit

In various embodiments, Compound 1 produced according to the methods described herein has one or more of the analytical parameters, including amounts of impurities, set forth in Table 11 or Table 12.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

ENUMERATED EMBODIMENTS

The following exemplary embodiments are provided, the numbering of which is not to be construed as designating levels of importance:

Embodiment 1 provides a method of making a compound of Formula I,

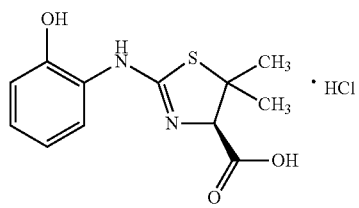

Formula I (Compound 1), the method comprising: reacting an amine compound with a structure of

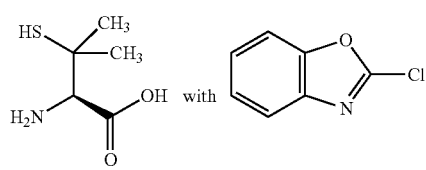

in the presence of a base and a first solvent to form an intermediate product of Formula II:

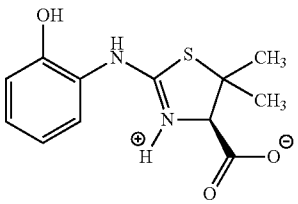

Formula II (Compound 1 Zwitterion); and contacting the intermediate product with an acid and a second solvent to form the compound of Formula I.

Embodiment 2 provides the method of embodiment 1, wherein the base comprises an alkali metal hydroxide.

Embodiment 3 provides the method of any one of embodiments 1-2, wherein the alkali metal hydroxide is selected from the group consisting of LiOH, NaOH, KOH, and any combination thereof.

Embodiment 4 provides the method of any one of embodiments 1-3, wherein the alkali metal hydroxide is NaOH.

Embodiment 5 provides the method of any one of embodiments 1-4, wherein the first solvent comprises a polar protic solvent, a polar aprotic solvent, or any combination thereof.

Embodiment 6 provides the method of any one of embodiments 1-5, wherein the first solvent is a polar protic solvent.

Embodiment 7 provides the method of any one of embodiments 1-6, wherein the first solvent is water.

Embodiment 8 provides the method of any one of embodiments 1-7, wherein the intermediate product of Formula II is isolated prior to contacting with the acid and the second solvent.

Embodiment 9 provides the method of any one of embodiments 1-8, wherein the acid is an inorganic acid or an organic acid.

Embodiment 10 provides the method of any one of embodiments 1-9, wherein the acid is an inorganic acid.

Embodiment 11 provides the method of any one of embodiments 1-10, wherein the acid is hydrochloric acid (HCl).

Embodiment 12 provides the method of any one of embodiments 1-11, wherein the compound of Formula I has an enantiomeric purity of at least about 98%.

Embodiment 13 provides the method of any one of embodiments 1-12, wherein the compound of Formula I comprises about 0.0001% to about 0.30% w/w of at least one impurity selected from the group consisting of 2-Cl-BO, BO-Imp-1, BO-Imp-2, BO-Imp-3, BO-Imp-4, BO-Imp-5, and Cmp1 Imp-3.

Embodiment 14 provides the method of any one of embodiments 1-13, wherein the compound of Formula I comprises about 0.010% to about 0.020% w/w of BO-Imp-1 and about 0.002% to about 0.004% w/w of BO-Imp-5.

Embodiment 15 provides a compound of Formula I:

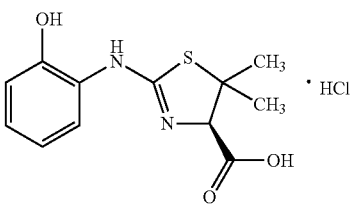

Formula I (Compound 1), comprising about 0.0001% to about 0.30% w/w of at least one impurity selected from the group consisting of 2-Cl-BO, BO-Imp-1, BO-Imp-2, BO-Imp-3, BO-Imp-4, BO-Imp-5, and Cmp1 Imp-3.

Embodiment 16 provides the compound of embodiment 15, which comprises about 0.010% to about 0.020% w/w of BO-Imp-1 and about 0.002% to about 0.004% w/w of BO-Imp-5.

Embodiment 17 provides the compound of any one of embodiments 15-16, which comprises about 0.01% to about 0.10% w/w of BO-Imp-1 and about 0.05% to about 0.3% w/w of Cmp1 Imp-3.

Embodiment 18 provides the compound of any one of embodiments 15-17, which has an enantiomeric purity of at least about 98%.

Embodiment 19 provides a pharmaceutical composition comprising the compound of any one of embodiments 15-18.

Embodiment 20 provides the pharmaceutical composition of embodiment 19, wherein the pharmaceutical composition comprises at least one pharmaceutically acceptable carrier.

Embodiment 21 provides a crystalline form of the compound of Formula I:

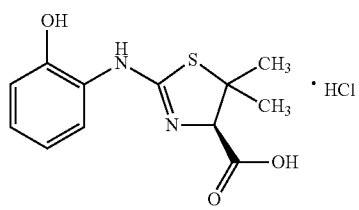

Formula I (Compound 1), wherein the crystalline form is characterized by an X-ray powder diffraction (XPRD) pattern comprising approximate peak positions (degrees 2θ±0.2), when measured using Cu Kα radiation, of 9.6, 15.2, 18.0, 19.4, 23.0, and 31.4, when the XPRD is collected from about 2 to about 42 degrees 2θ.

Embodiment 22 provides the crystalline form of embodiment 21, wherein the crystalline form is characterized by an XPRD pattern comprising approximate peak positions (degrees 2θ±0.2) of 9.6, 15.2, 15.8, 17.5, 18.0, 19.4, 21.9, 23.0, 24.5, 25.1, 26.4, and 31.4.

Embodiment 23 provides the compound of anyone of embodiments 15-18, which comprises less than 0.05% w/w of each of BO-Imp-2, BO-Imp-3, BO-Imp-4, and BO-Imp-5.

What is claimed is:
1. A composition comprising a compound of Formula I:

Formula I

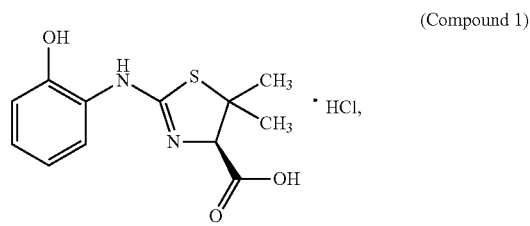

(Compound 1)

wherein the composition comprises about 0.0001% to about 0.004% w/w, relative to the weight of Compound 1 in the composition, of each of:
2-Cl-BO (2-Chlorobenzoxazole),
BO-Imp-3 (2-Aminophenol), and
BO-Imp-4 (2-[Bis(1,3-benzoxazol-2-yl) amino]phenol).

2. The composition of claim 1, wherein the compound of Formula I is present at an enantiomeric purity of at least about 98% in the composition.

3. The composition of claim 1, wherein the composition further comprises at least one pharmaceutically acceptable carrier.

4. A crystalline form of the compound of Formula I:

Formula I

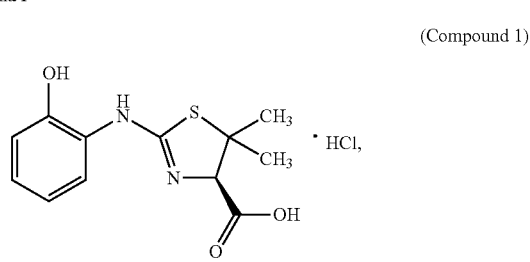

(Compound 1)

wherein the crystalline form is characterized by an X-ray powder diffraction (XPRD) pattern comprising approximate peak positions (degrees 2θ±0.2), when measured using Cu $K_\alpha$ radiation, of 9.6, 15.2, 18.0, 19.4, 23.0, and 31.4, when the XPRD is collected from about 2 to about 42 degrees 2θ.

5. The crystalline form of claim 4, wherein the crystalline form is characterized by an XPRD pattern comprising approximate peak positions (degrees 2θ±0.2) of 9.6, 15.2, 15.8, 17.5, 18.0, 19.4, 21.9, 23.0, 24.5, 25.1, 26.4, and 31.4.

6. A composition comprising the crystalline form of claim 4 and at least one pharmaceutically acceptable carrier.

* * * * *